United States Patent
Bibette et al.

(10) Patent No.: US 10,710,045 B2
(45) Date of Patent: Jul. 14, 2020

(54) CAPSULES CONTAINING MAMMALIAN CELLS

(71) Applicants: Jerome Bibette, Paris (FR); Nicolas Atrux-Tallau, Antibes (FR); Hugo Domejean, Paris (FR); Anette Funfak, Paris (FR); Nicolas Bremond, Paris (FR); Pierre Nassoy, Villenave d'Ornon (FR); Kevin Alessandri, Geneva (CH)

(72) Inventors: Jerome Bibette, Paris (FR); Nicolas Atrux-Tallau, Antibes (FR); Hugo Domejean, Paris (FR); Anette Funfak, Paris (FR); Nicolas Bremond, Paris (FR); Pierre Nassoy, Villenave d'Ornon (FR); Kevin Alessandri, Geneva (CH)

(73) Assignee: CAPSUM, Marseilles (FR)

( * ) Notice: Subject to any disclaimer, the term of this patent is extended or adjusted under 35 U.S.C. 154(b) by 929 days.

(21) Appl. No.: 14/375,612

(22) PCT Filed: Jan. 31, 2013

(86) PCT No.: PCT/EP2013/051976
§ 371 (c)(1),
(2) Date: Jul. 30, 2014

(87) PCT Pub. No.: WO2013/113855
PCT Pub. Date: Aug. 8, 2013

(65) Prior Publication Data
US 2015/0017676 A1 Jan. 15, 2015

(30) Foreign Application Priority Data
Jan. 31, 2012 (FR) ...................................... 12 50875

(51) Int. Cl.
*G01N 33/50* (2006.01)
*B01J 13/22* (2006.01)
*B01J 13/08* (2006.01)
*B01J 13/10* (2006.01)

(52) U.S. Cl.
CPC .............. *B01J 13/22* (2013.01); *B01J 13/08* (2013.01); *B01J 13/10* (2013.01); *G01N 33/5008* (2013.01); *G01N 2500/10* (2013.01); *Y10T 428/2987* (2015.01)

(58) Field of Classification Search
CPC . B01J 13/08; B01J 13/10; B01J 13/22; G01N 2500/10; G01N 33/50; G01N 33/5008; Y10T 428/2987
USPC .................................................... 435/174, 29
IPC ...................................................... G01N 33/50
See application file for complete search history.

(56) References Cited

U.S. PATENT DOCUMENTS

| 3,733,205 A * | 5/1973 | Shovers ................. C12H 1/003 426/12 |
| 4,409,331 A | 10/1983 | Lim |
| 5,459,054 A * | 10/1995 | Skjak-Braek ........ A61K 9/1652 424/422 |
| 2004/0013738 A1* | 1/2004 | Voigt et al. ................... 424/490 |
| 2007/0275080 A1* | 11/2007 | Laulicht .................. B01J 13/08 424/493 |
| 2012/0003285 A1 | 1/2012 | Bibette et al. |

FOREIGN PATENT DOCUMENTS

| FR | 2 939 012 A | 6/2010 |
| FR | 2 955 257 A1 | 7/2011 |
| GB | 2 145 992 A | 4/1985 |
| WO | 92/05778 A1 | 4/1992 |
| WO | WO03055990 A2 * | 7/2003 ............... C12N 5/02 |
| WO | 2011/072557 A | 6/2011 |

OTHER PUBLICATIONS

Lanza et al. Encapsulated cell technology. Nature Biotechnology, vol. 14 Sep. 1996, pp. 1107-1111.*
U.S. Appl. No. 15/103,655.*
https://www.google.com/?gws_rd=ssl, (printed Jul. 8, 2016.*
Nicodemus et al. 2008. Cell Encapsulation in Biodegradable Hydrogels for Tissue Engineering Applications. Tissue Engineering: Part B vol. 14, No. 2, pp. 149-165.*
Tong et al. 2008. Multilayer microcapsules with tailored structures for bio-related Applications. Journal of Materials Chemistry, vol. 18, pp. 3799-3812.*
Maguire et al., 2005. Biotechnology and Bioengineering, vol. 93, pp. 581-591.*
Hunt N. et al., "Cell encapsulation using biopolymer gels for regenerative medicine", Biotechnology Letters, 2010, vol. 32, No. 6, pp. 733-742. (Year: 2010).*
Database WPI Week 201145 Thomson Scientific. London. GB; AN 2011-H11466 XP002712352, & WO 2011/072557 A1 (CAS Dalian Chem&Physical Inst) Jun. 23, 2011 (Jun. 23, 2011) abstract.
Nicolas Bremond et al.: "Formation of liquid-core capsules having a thin hydrogel membrane: liquid pearls", Soft Matter, vo 1. 6. No. 11. Jan. 1, 2010 (Jan. 1, 2010). p. 2484, XP055072164, ISSN: 1744-683X. DOi: 10.1039/b923783f p. 2484-p. 2485 figures 1-6.
International Search Report, dated Jan. 10, 2014, from corresponding PCT application.

* cited by examiner

*Primary Examiner* — Satyendra K Singh
(74) *Attorney, Agent, or Firm* — Young & Thompson

(57) ABSTRACT

A capsule containing at least one mammalian cell, includes a liquid core, and at least one external envelope totally encapsulating the liquid core at its periphery, the external envelope including at least one gelled polyelectrolyte and/or a stiffened biopolymer and being able to retain the liquid core when the capsule is immersed in a gas. The present invention further relates to the method for preparing such a capsule, to a method for screening cosmetic active ingredients as well as a culture method using such capsules.

13 Claims, 13 Drawing Sheets

CAPSULES CONTAINING MAMMALIAN CELLS

The present invention relates to a capsule allowing the growth of at least one cell of mammals, said capsule being formed with a liquid core and at least one external envelope totally encapsulating the liquid core at its periphery, to the method for preparing such a capsule, to a method for screening active ingredients as well as to a cultivation method using such capsules.

In all multicellular organisms, the cells are intrinsically found in a three-dimensional (3D) environment, represented by the neighbouring cells and the extra-cellular matrix (ECM). Even if the vast majority of cell biology studies in vitro are always conducted by using cell monolayers cultivated on flat substrates, more and more data show that two-dimensional (2D) cell cultures do not manage to reproduce the architecture of living tissues and, accordingly may bias the cell response to external signals or to integrated signals in the cell. In particular, it is believed that the poor predictability of the tissue response to novel cosmetic or therapeutic agents which were evaluated on cell monolayers is due to the absence of properties specific to the tissues of 2D cultivations. Since the 80s, multicellular spheroids (MCS) have been proposed as in vitro avascular solid microtumours in 3D, and the MCSes incorporated in or deposited on gels of the ECM type have further been used for studying the mechanisms of cell invasion. In biomedical research, these tests based on MCSes today represent a promising alternative which overcomes the limits of 2D cell cultures and thus avoids resorting to systematic tests in animals, provided that standardised preparation procedures are available and compatible with platforms of therapeutic tests. In parallel, the advances achieved in biological engineering and particularly in tissue engineering, give the possibility of reconstructing in vitro, a large variety of normal biological tissues, containing one or several types of cells. As an example, the reconstruction of skin tissue is currently achieved and successfully for therapeutic purposes, notably for grafting skin in treating persons burned to the third degree or chronic wounds. These reconstructed skins are also used in cosmetic research as an alternative method to animal experimentation, but also in dermo-pharmaceutical research. The use of reconstructed tissues represents a model of choice since the cells are in an environment similar to the environment encountered in vivo, the biological responses are therefore consistent with the in situ responses. However, the preparation of these biological tissues as well as their handling remain time consuming and complex. Significant advances have already allowed the design of a reconstructed or synthetic ECM based on self-assembly of fibrillar networks consisting of tailor-made polymers. The formation of MCSes is always generally achieved by using conventional methods such as the technique of the suspended drop, gyratory rotation or cultivations on a liquid layer, the main drawbacks of which are their low yield and the difficulty of controlling the size of the cell aggregates. The arrival of photolithography at a microscopic scale has recently led to diverse sophisticated attempts as regards automated production of MCSes by means of micro-networks, micro-wells or micro-fluidic devices. On the other hand, these emerging techniques have not developed beyond the proof of concept, notably because of problems of practicability and of the difficulty of obtaining delicate cell cultivation conditions. Nevertheless, these techniques relate to capsules of very small sizes of the order of about 10 microns and remain expensive. Further, the capsules described by the prior art do not generally allow rapid and massive production (of the industrial type) of hollow, permeable and elastic shells, containing cells and having a controlled size.

Moreover, the prior art describes beads containing cells, these are spherical structures consisting of a solid core (solid sphere). The absence of a liquid core reduces the field of application of these beads since the cells are in an entanglement of polymer and are separated from each other by the polymer. Thus, these cells can only colonise the entanglement and therefore cannot be organised in another form, for example in order to form a pluristratified epithelial type structure.

The applicant has described capsules which may contain cells (FR 2 939 012). Nevertheless, the application does not mention that the capsules are suitable for encapsulation and the cultivation of eukaryotic mammalian cells which because of their greater fragility, are cells which are difficult to cultivate.

In this context, the main goal of the invention consists of developing a novel simple and reproducible method for obtaining a preparation with a high throughput of capsules having a controlled size, the peripheral wall of which is biocompatible, and sufficiently permeable for allowing the passage of nutrients and for which the elastic properties do not cause any cellular stress which may inhibit the growth of eukaryotic mammalian cells. The goal of the invention consists of developing a novel, simple and reproducible method for obtaining a preparation with a high throughput of compartmented capsules or not allowing a choice of culture of eukaryotic mammalian cells in suspension and/or in spheroids and/or in tissues and notably allowing three-dimensional cultivation of eukaryotic mammalian cells and therefore the setting up of tissue models, interaction models between several cell types, biological barrier models such as the dermo-epidermal junction.

The invention relates to a capsule comprising a liquid core, and at least one external envelope totally encapsulating the liquid core at its periphery, said external envelope being able to retain the liquid core when the capsule is immersed into a gas and comprising at least one gelled polyelectrolyte and/or a stiffened biopolymer, said capsule comprising at least one eukaryotic mammalian cell.

The capsules according to the invention have a simple and effective preparation, and allow long-term cultivation of eukaryotic cells as well as the obtaining of three-dimensional culture models for notably high flow rate screening in physiologically relevant 3D environments.

Indeed, the inventors have demonstrated that the capsules according to the invention allow good growth of the mammalian cells in spite of the confinement related to encapsulation. Thus, the elastic characteristics of the capsule are sufficient for allowing deformation of the envelope so that the cell culture reaches confluence while retaining its integrity, thus avoiding bursting of the capsule.

Further, the inventors have shown that the capsule allows adhesion of the cells thereby improving their growth and their survival.

The inventors have moreover demonstrated that these capsules give the possibility of generating tissue models such as models of the skin, of the epidermis or of the dermis.

The invention also relates to a method for preparing a capsule comprising the following steps:
  a) forming a multi-component liquid drop comprising:
    a liquid core comprising at least one eukaryotic cell preferably of a mammal, and a liquid external envelope formed with an aqueous composition comprising at least one polyelectrolyte and at least one surfactant, totally encapsulating at its periphery the liquid core,
b) gelling by immersion of said multi-component liquid drop in a gelling solution containing a reagent capable of gelling the polyelectrolyte of the liquid external envelope, in order to obtain a gelled capsule comprising a gelled external envelope, and
c) recovering said gelled capsules,
or
a) forming a multi-component liquid drop comprising:
a liquid core,
a liquid intermediate envelope formed with an aqueous composition comprising at least one biopolymer, totally encapsulating at its periphery the liquid core, and
a liquid external envelope formed with an aqueous composition different from the intermediate composition, said aqueous composition comprising at least one polyelectrolyte and at least one surfactant, said liquid external envelope totally encapsulating at its periphery the intermediate envelope, the liquid core and/or the liquid intermediate envelope comprising at least one eukaryotic cell, preferably of a mammal,
b) gelling by immersion of said multi-component liquid drop in a gelling solution containing a reagent capable of gelling the polyelectrolyte of the liquid external envelope, in order to obtain a gelled capsule comprising a gelled external envelope,
c) stiffening the intermediate composition of the liquid intermediate envelope, in order to obtain a gelled and stiffened capsule comprising a stiffened intermediate envelope, and
d) recovering said gelled and stiffened capsules.

The invention also deals with a method for screening cosmetic active ingredients comprising:
a) the cultivation of a capsule according to the invention in the presence and in the absence of a candidate substance,
b) the detection of a phenotype of interest in the cells of the cultivated capsule in the presence of the candidate substance as compared with the cells of the cultivated capsule in the absence of the candidate substance, and
c) identifying the substance as an active ingredient if a phenotype of interest has been detected.

The invention further relates to the use of a capsule according to the invention for in vitro cultivation of eukaryotic mammalian cells.

The invention further relates to an in vitro method for cultivating eukaryotic cells of the mammalian comprising the following steps:
a) cultivating a capsule according to the invention under sufficient conditions for cell growth, and
b) harvesting said capsule.

The present invention finally relates to a method for storing eukaryotic mammalian cells comprising the manufacturing of a capsule according to the method of the invention, and to a step for storing said obtained capsules.

Method for Preparing a Capsule

The present invention relates to a method for preparing a capsule comprising the following steps:
a) forming a multi-component liquid drop comprising:
a liquid core comprising at least one eukaryotic cell, preferably of a mammal, and
a liquid external envelope formed with an aqueous composition or if necessary oily composition, comprising at least one polyelectrolyte and at least one surfactant, totally encapsulating at its periphery the liquid core,
b) gelling by immersion of said multi-component liquid drop in a gelling solution containing a reagent capable of gelling the polyelectrolyte of the liquid external envelope, in order to obtain a gelled capsule comprising a gelled external envelope, and
c) recovering said gelled capsules,
or
a) forming a multi-component liquid drop comprising:
a liquid core,
a liquid intermediate envelope formed with an aqueous or if necessary oily composition comprising at least one biopolymer, totally encapsulating at its periphery the liquid core, and
a liquid external envelope formed with an aqueous composition, different from the intermediate composition, said aqueous or if necessary oily composition comprising at least one polyelectrolyte and at least one surfactant, said liquid external envelope totally encapsulating at its periphery the intermediate envelope, the liquid core and/or the liquid intermediate envelope comprising at least one eukaryotic cell, preferably of a mammal,
b) gelling by immersion of said multi-component liquid drop in a gelling solution containing a reagent capable of gelling the polyelectrolyte of the liquid external envelope, in order to obtain a gelled capsule comprising a gelled external envelope,
c) stiffening the intermediate composition of the liquid intermediate envelope, in order to obtain a gelled and stiffened capsule comprising a stiffened intermediate envelope, and
d) recovering said gelled and stiffened capsules.

Within the scope of the present description, by «gelled capsule» is meant a capsule comprising a liquid core and a gelled envelope. Advantageously, the gelled capsule does not comprise any stiffened envelope, but may comprise a liquid intermediate envelope. A gelled capsule according to the invention may comprise at least one eukaryotic cell, preferably of a mammal in the liquid core. When the gelled envelope and if necessary the liquid envelope comprise a biopolymer, they may include independently of each other, at least one eukaryotic mammalian cell.

Within the scope of the present description, by «gelled and stiffened capsule» is meant a capsule comprising a liquid core, a gelled envelope and a stiffened envelope. Advantageously, the gelled envelope totally encapsulate at its periphery the stiffened envelope, which itself totally encapsulates at its periphery the liquid core. A gelled and stiffened capsule according to the invention may comprise at least one eukaryotic mammalian cell in the liquid core and/or in the stiffened envelope, when the gelled envelope comprises a biopolymer.

Within the scope of the present description, by «aqueous composition» is meant a composition having the property of solubilising polar compounds.

Within the scope of the present description, by «oily composition» is meant a composition having the property of solubilising apolar compounds, such as fats, oils or lipids.

An oily composition, also called a hydrophobic composition, is insoluble in water. It preferably comprises a fat, an oil or a mixture of oils of plant, animal or mineral origin.

As a plant oil, mention may for example be made of sweet almond oil, jojoba oil, palm oil or phytosqualane.

As fats, mention may be made for example of fatty alcohols and/or fatty acid esters, typically $C_1$-$C_{20}$ esters, such as isopropyl myristate, glycerol myristate, isononyl isononanoate, triglycerides of caprylic acid or of capric acid, isopropyl palmitate and ethyl palmitate. Mention may also be made of silicone oils or polysiloxanes, such as polydimethylsiloxanes (PDMS).

As an animal oil, mention may for example be made of squalene.

As a mineral oil, mention may be made for example of hydrogenated polyisobutylene, isododecane or paraffinic oils.

The liquid core generally consists of an internal generally liquid or slightly viscous composition, which may be aqueous or oily. The liquid core, intended to be encapsulated and which may contain at least one eukaryotic mammalian cell preferentially has a composition allowing cell survival, regularisation of the pH such as a buffer. The core is generally liquid or slightly viscous, it is preferentially iso-osmotic and does not contain any compounds which are not compatible with gelling and/or stiffening.

The intermediate envelope is formed with an intermediate aqueous or if necessary oily composition typically consisting of a latex of polymers, such as a natural latex notably a biopolymer. By «biopolymer», is meant a polymer of natural origin and/or a biocompatible polymer or a polymer comprising a fragment of such a polymer. A polymer of natural origin is preferentially a polymer naturally present in mammalian eukaryotes. A biocompatible polymer is a synthetic polymer identical with a polymer of natural origin or a synthetic polymer which does not interact in a negative way with the cells and allow their survival. A biopolymer may comprise proteins and/or polysaccharides and/or fatty acids and/or nucleic acids or fragments thereof. A biopolymer suitable for the invention may be selected from proteins of the extra-cellular matrix, proteoglycans, glycosaminoglycans (GAGs), polysaccharides and their non-hydrolysed or partly hydrolysed form. The proteins notably of the extra-cellular matrix and their non-hydrolysed or partly hydrolysed form are selected from collagens, gelatine, fibronectin, elastin, poly-L-Lysine, laminin and derivatives thereof. Proteoglycans are selected from decorin (chondroitin-sulfate/dermatan-sulfate), perlecan (heparane-sulfate) and aggrecan and derivatives thereof. The glycosaminoglycans are selected from heparin, hyaluronic acid, keratane sulfate, heparane sulfate, chondroitin sulfate, dermatane sulfate and derivatives thereof. The polysaccharides are selected from inulin, graminan, levan, starch, amylopectin, amylose, cellulose, curdlan, dextrins, glycogen, pullulan, beta-glucan, agar-agar, carrageenans, chitin, chitosan, mannans, xylanes. Preferentially, the biopolymer is selected from collagen, gelatin, laminin, entractin, at least one GAG such as heparane sulfate or their mixture.

The external envelope is formed with an external aqueous composition, comprises at least one polyelectrolyte and at least one surfactant. Said polyelectrolyte may be different from or identical with the biopolymer of the intermediate envelope.

When the liquid core or the intermediate envelope is intended to contain eukaryotic mammalian cells, the internal composition, the intermediate composition or the external composition is adapted for allowing cell survival. For example, it contains a physiological buffer such as a Hepes buffer or a culture medium such as RPMI, DMEM or MEM. Preferentially, the internal composition, the intermediate composition or the external composition have a pH between 7.2 and 7.4. Preferentially, the liquid core and/or the intermediate envelope comprises $10^3$ to $10^9$ eukaryotic mammalian cells/mL. Typically, the liquid core comprises $10^6$ cells/mL, the intermediate composition comprises $0.75 \cdot 10^6$ cells/mL.

Further, the liquid core and/or the intermediate envelope comprise, 1 to $10^7$ cells, preferentially, 5 to $10^6$, 30 to $5 \cdot 10^5$, 50 to $10^5$, 35 to $5 \cdot 10^4$, 100 to $10^4$, 150 to $10^4$, 200 to $10^3$ eukaryotic mammalian cells.

According to the invention, the liquid core and/or the intermediate envelope comprises or does not comprise any chelating agents or phosphates.

Within the scope of the present invention, by «multi-component drop» is meant a liquid drop consisting of at least one liquid central core and of a liquid external envelope totally encapsulating at its periphery the liquid central core. Preferentially, the «multi-component drop» is a liquid drop consisting of a liquid central core, of a liquid intermediate envelope, totally encapsulating at its periphery the liquid core, and a liquid external envelope totally encapsulating at its periphery the liquid intermediate envelope. In this second alternative, the intermediate envelope is in contact with the core and with the external envelope and maintains the core out of contact with the external envelope. According to another alternative, the «multi-component drop» may comprise more than two envelopes.

Preferentially, the intermediate composition, at the interface between the external composition and the internal composition has a lower viscosity than that of the external composition and greater than that of the internal composition. One skilled in the art easily knows how to balance their viscosity according to the composition of each of the layers, in order to obtain such variations.

The viscosity may be measured according to the invention, by means of a Brookfield RVT viscosimeter at 20° C. by following the indications of the manufacturer.

Step for Forming a Multi-Component Liquid Drop

The production of this type of drop is generally carried out by co-extrusion of different compositions, i.e. the internal composition, if necessary, the intermediate composition, and the external composition, as defined in the aforementioned method.

Preferentially, the internal composition and/or the intermediate composition are aqueous or if necessary oily.

The production of multi-component drops by co-extrusion may be accomplished for example by separate conveyance in a double or triple envelope. The method may be explained hereafter for a multi-component drop by co-extrusion of three compositions, nevertheless, the principle remains applicable for two compositions or more.

In the case of a triple envelope of three flows: a first flow consisting of the internal composition, a second flow consisting of the intermediate composition and a third flow consisting of the external composition, as described in application FR 1061404 (FIG. 6).

At the outlet of the triple envelope, the three flows come into contact and then form a multi-component drop, according to a hydrodynamic, so called «dripping» mode (drop wise, as notably described in WO 2010/063937) or so called «jetting» hydrodynamic mode (formation of a liquid jet at the outlet of the triple envelope, as notably described in FR 10 56925). The first flow is the liquid core, the second flow is the liquid intermediate envelope and the third flow is the liquid external envelope.

According to the production mode, each multi-component drop is detached from the triple envelope and falls in a volume of air, before being immersed in a gelling solution S1 containing a reagent capable of gelling the polyelectrolyte of the liquid external envelope, in order to form the gelled external envelope of the capsules according to the invention (FIG. 6).

According to certain alternatives, the multi-component drops may comprise additional layers between the external envelope and the liquid core, other than the intermediate envelope. This type of drop may be prepared by separate conveyance of multiple compositions in devices with multiple envelopes.

Gelling Step

When the multi-component drop comes to the contact with the gelling solution, the reagent capable of gelling the polyelectrolyte present in the gelling solution then forms bonds between the different polyelectrolyte chains present in the liquid external envelope, then passing to the gelled state, thus causing gelling of the liquid external envelope.

Without intending to be bound to a particular theory, during the passing to the gelled state of the polyelectrolyte, the individual polyelectrolyte chains present in the liquid external envelope join up with each other in order to form a cross-linked lattice, also called a hydrogel.

Within the scope of the present description, the polyelectrolyte present in the gelled external envelope is in the gelled state and is also called a polyelectrolyte in the gelled state or further a gelled polyelectrolyte.

A gelled external envelope, capable of retaining the core of the capsule and if necessary, the assembly formed by the core and the intermediate envelope is thereby formed. This gelled external envelope has a specific mechanical strength, i.e. it is capable of totally surrounding the intermediate envelope and of retaining the core encapsulated by this intermediate envelope. This has the effect of maintaining the internal structure of the core liquid and of the intermediate envelope.

Generally, the gelled external envelope appears as a monolayer envelope, totally encapsulating the intermediate envelope at its periphery.

The capsules according to the invention dwell in the gelling solution for the time during which the external envelope is completely gelled.

The gelled capsules may then optionally be collected and immersed in an aqueous rinsing solution, generally essentially consisting of water, of a physiological buffer and/or of a culture medium in order to rinse the formed gelled capsules. This rinsing step allows extraction of the gelled external envelope, a possible excess of the reagent of the gelling solution capable of gelling, and all or part of the surfactant (or of other species) initially contained in the external aqueous composition.

The presence of a surfactant in the external aqueous composition allows improvement in the formation and gelling of the multi-component drops according to the method as described earlier.

The polyelectrolyte of the gelled external envelope of the capsules according to the invention is advantageously selected from polyelectrolytes which react to multivalent ions.

Within the scope of the present description, by «polyelectrolyte reacting to multivalent ions» is meant a polyelectrolyte which may pass from a liquid state in an aqueous solution to a gelled state under the effect of a contact with a gelling solution containing multivalent ions, such as ions of an earth-alkaline metal for example selected from calcium, barium or magnesium ions.

In the liquid state, the individual polyelectrolyte chains are substantially free to flow relatively to each other. A 2% by mass aqueous solution of polyelectrolyte then has a purely viscous behaviour at the shearing gradients characteristic of the shaping method. The viscosity of this solution with zero shearing is between 50 mPa·s and 10000 mPa·s, advantageously between 3000 mPa·s and 7000 mPa·s.

The individual polyelectrolyte chains in the liquid state advantageously have a molar mass of more than 65,000 g/moles.

Said gelling solution 51 is for example an aqueous solution of a salt of the $X_n M_m$ type wherein X is for example a halide ion such as a chloride, bromide, iodide or fluoride ion, or else further a tartrate ion, and M is advantageously a multivalent cation of an earth-alkaline element such as calcium, magnesium or barium and n and m are greater than or equal to 1.

The concentration of salt of the $X_n M_m$ type in the gelling solution is advantageously comprised from 5% to 20% by mass.

In the gelled state, the individual polyelectrolyte chains form, with the multivalent ions, a coherent three-dimensional lattice which retains the core and the intermediate envelope and prevents its flowing. The individual chains are retained relatively to each other and cannot freely flow relatively to each other. Further, the gel has a flow stress threshold. This stress threshold is greater than 0.05 Pa. The gel also has a non-zero elastic modulus and greater than 35 kPa.

The polyelectrolyte is preferably a biocompatible polymer selected from polysaccharides, synthetic polyelectrolytes based on acrylates (sodium, lithium, potassium or ammonium polyacrylate, or polyacrylamide), or synthetic polyelectrolytes based on sulfonates (sodium poly(styrene sulfonate), for example).

Preferably, the polyelectrolyte is selected from polysaccharides reacting to multivalent ions, preferentially food polysaccharides.

More particularly, the polyelectrolyte is selected from alkaline alginates such as sodium alginate or potassium alginate, gellans and pectins.

In the case when the polyelectrolyte is a sodium alginate (NaAlg), and when the reagent is calcium fluoride, the reaction which occurs during gelling is the following:

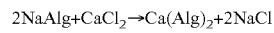

$$2NaAlg + CaCl_2 \rightarrow Ca(Alg)_2 + 2NaCl$$

The alginates are produced from brown *algae* called «laminaria», designated by the term of «sea weed».

Preferably, the polyelectrolyte is an alkaline alginate advantageously having a bulk content of α-L-guluronate of more than 50%, notably more than 55%, or even more than 60%.

The polyelectrolyte is for example, a sodium alginate.

According to a preferred embodiment, the total mass percentage of polyelectrolyte in the gelled external phase is comprised from 0.5% to 5%, preferably less than 3%.

The total mass percentage of polyelectrolyte in the gelled external phase is for example equal to 2%.

Stiffening Step

During the method according to the invention, when the capsule comprises an intermediate envelope, the method further comprises a step for stiffening the intermediate composition. The gelled capsules obtained at the end of the gelling step, optionally rinsed, are then subject to a step for stiffening the intermediate composition. Preferably, the stiffening step is concomitant with that of gelling. The concomitance of both of these steps is of interest in order to avoid flowing of the intermediate composition and its accumulation in a portion of the capsule and therefore the formation of a non-uniform intermediate envelope.

With the stiffening step of the method of the invention, the elastic modulus of the intermediate envelope becomes non-zero.

The intermediate composition comprises at least one biopolymer alone or mixed with a polymer or a mixture of polymers and/or a monomer or a mixture of monomers, optionally present in the form of a colloidal dispersion.

Within the scope of the present invention, the liquid intermediate envelope may be stiffened according to any stiffening method which may be contemplated, such as for example by polymerisation, by precipitation, by colloidal aggregation or else by a glassy transition generally caused by a variation in temperature.

In order to carry out this step, the gelled capsules are generally immersed in a stiffening bath.

According to a first alternative, the stiffening bath corresponds to the gelling solution used during the gelling step. Advantageously, the capsules are gelled and then stiffened in the gelling solution.

According to another alternative, the stiffening bath is different from the gelling solution, and it is therefore generally necessary to collect the gelled capsules, and optionally rinse them, and then immerse them in the stiffening bath for carrying out the stiffening step.

The stiffening step is typically carried out by coacervation of the intermediate composition of the liquid intermediate envelope.

The stiffening, notably by coacervation is achieved in the presence of the external envelope and through the latter, after its gelling. The external envelope therefore plays the role of an external mould for making the stiffened intermediate envelope.

According to this embodiment, the coacervation of the intermediate composition of the intermediate envelope causes stiffening of said liquid envelope, which has the advantage of imparting greater mechanical strength to said capsules.

Within a coacervate comprising at least one biopolymer, the bonds binding the polymer chains together are generally of the ionic type, and are generally stronger than bonds present within a membrane of the surfactant type.

Several coacervation methods for the intermediate composition may be used.

According to a first embodiment, the coacervation of the intermediate composition is caused by a variation of temperature or of the pH, or by electromagnetic radiation.

According to this embodiment, the stiffening bath does not generally comprise any stiffening agent, but induces coacervation by a variation of the reaction conditions, which may correspond to a change in the temperature, in the pH or to concentration or dilution conditions, or to application of UV or IR radiation, preferably by a change of the temperature.

The biopolymer adapted to this first embodiment may be selected from biopolymers, for which the viscosity varies according to temperatures such as glycans, glycoproteins or proteins, such as those intended to form extracellular biological matrices. A biopolymer suitable for the invention may be selected from proteins notably of the extracellular matrix, proteoglycans, glycosaminoglycans, polysaccharides and their non-hydrolysed or partly hydrolysed form. Preferentially, the biopolymer is selected from collagen, gelatin, laminin, entractin, at least one GAG such as heparane sulfate or their mixture. As an example of a biopolymer suitable for the invention, mention may be made of Geltrex™ which is liquid at low temperature and becomes elastic at 37° C. after 30 minutes of incubation or Matrigel™, which is liquid at low temperature and becomes elastic at room temperature, or else collagen which gels at low temperature.

According to another embodiment, the coacervation of the biopolymer is carried out by coacervation with a multivalent cation.

According to first alternative, the multivalent cations are contained in the stiffening bath (or optionally in the gelling solution) and diffuse through the gelled external envelope in order to react with the biopolymer and form a coacervate.

The hydrogel making up the gelled external envelope is generally sufficiently permeable for allowing permeation of multivalent cations.

As a biopolymer adapted to this first alternative, for example, a hydrophilic polyelectrolyte, more particularly a polysaccharide (however different from or identical with the polyelectrolyte of the gelled external envelope) may be noted.

As a biopolymer also adapted to this first alternative, it is possible to mention natural latex, in the form of a colloidal dispersion of polymers. A multivalent cation adapted to this embodiment is for example a cation of an earth-alkaline element such as calcium, magnesium or barium.

According to another embodiment, the coacervation of the intermediate composition is carried out by coacervation with a second reagent R2, different from the biopolymer R1.

According to a first alternative, the second reagent R2 is contained in the stiffening bath (or optionally in the gelling solution) and diffuses through the gelled external envelope in order to react with the biopolymer R1 and form a coacervate.

The hydrogel making up the gelled external envelope is generally sufficiently permeable for allowing permeation of such polymers.

According to another alternative, the second reagent R2 is contained in the intermediate composition forming the liquid intermediate envelope even before the immersion in the stiffening bath, and, during the immersion in the stiffening bath, a variation of the temperature or pH conditions causes coacervation of the biopolymer R1 with said second reagent R2.

The formation of the coacervate between the biopolymer R1 and the second reagent R2 is generally caused by a variation of the conditions of the reaction medium (temperature, pH, concentration of reagents, etc.), generally caused by immersion in the stiffening bath.

Typically, the biopolymer R1 and the second reagent R2 are charged polymers with opposite charges.

In this case, the coacervation reaction results from the neutralisation of the biopolymer R1 and of the second reagent R2 charged with opposite polarities, and allows the formation of a membrane structure stiffened by electrostatic interactions between the biopolymer R1 and the second reagent R2. The stiffened intermediate envelope thus form around the liquid core encapsulates it totally and isolates it from the outside, and notably from the gelled external envelope.

Preferably, the biopolymer R1 is a charged polymer (or polyelectrolyte) of the anionic or cationic type.

Preferably, the second reagent R2 is a charged polymer (or polyelectrolyte) with a charge opposite to the biopolymer R1, of the cationic or anionic type, preferably hydrophilic.

According to other alternatives, the biopolymer R1 is a mixture of polymers charged with the same polarity.

According to other alternatives, the second reagent R2 is a mixture of polymers charged with the same polarity, but with a polarity opposite to that of the biopolymer R1.

According to another embodiment, the biopolymer R1 is a monomer or a mixture of monomers, capable of polymerising with the second reagent R2, as a polymer or monomer, optionally in the presence of a polymerisation agent.

Said second reagent R2 may be present in the stiffening bath and passed through the permeable gelled external envelope in order to polymerise with the biopolymer R1.

Alternatively, the second reagent R2 may be present in the intermediate composition, and the polymerisation is caused by the permeation of a polymerization agent, contained in the stiffening bath.

In both cases, the coacervation of the intermediate envelope is due to the polymerisation of the biopolymer R1 and of the second reagent R2.

As a biopolymer R1 and as a second reagent R2, mention may be made for example of monomers capable of forming cocacervates of polyurethanes, such as polyisocyanates and polyols, or further monomers capable of forming polyacrylamide cocacervates.

According to a first alternative, the biopolymer R1 is a hydrophilic anionic polymer and the second reagent R2 is a hydrophilic cationic polymer.

According to this alternative, the intermediate composition comprising the hydrophilic anionic biopolymer R1 is an aqueous composition.

According to this alternative, the second reagent R2, is a hydrophilic cationic polymer which may be contained if necessary in an aqueous stiffening bath or else in the aqueous intermediate composition.

As a biopolymer R1 is suitable for this alternative, mention may be made for example of polyacrylic acid, polysaccharides.

As a second reagent R2 suitable for this alternative, mention may be made for example of gelatin, chitosan.

According to another alternative, the biopolymer R1 is a hydrophilic cationic polymer and the second reagent R2 is a hydrophilic anionic polymer.

According to this alternative, the intermediate composition comprising the hydrophilic cationic biopolymer R1 is an aqueous composition.

According to this alternative, the second hydrophilic anionic reagent R2, may be contained in an aqueous stiffening bath or else in the aqueous intermediate composition.

As a biopolymer R1 suitable for this alternative, mention may for example be made of gelatin, chitosan.

As a second reagent R2 suitable for this alternative, mention may be made for example of polyacrylic acid, polysaccharides.

According to another alternative, the biopolymer R1 is a lipophilic cationic polymer and the second reagent R2 is a hydrophilic anionic polymer.

According to this alternative, the intermediate composition comprising the lipophilic cationic biopolymer R1 is an oily composition.

According to this alternative, the second anionic lipophilic reagent R2 is contained in an oily stiffening bath.

As a biopolymer R1 suitable for this alternative, mention may for example be made of aminosilica.

As a second reagent R2 suitable for this alternative, mention may be made for example of polyacrylic acid.

Within the scope of the present description, by «polymer of the anionic type» or «anionic polymer» is meant a polymer including chemical functions of the anionic type. It may also be referred to as an anionic polyelectrolyte.

By «chemical function of the anionic type», is meant a chemical function AH capable of yielding a proton in order to obtain a function A. Depending on the conditions of the medium in which it is found, the polymer of the anionic type therefore includes chemical functions in the form of AH, or else in the form of its conjugate base A.

As an example of chemical functions of the anionic type, mention may be made of carboxylic acid functions —COOH, optionally present in the form of a carboxylate anion —COO$^-$.

As an example of polymer of the anionic type, mention may be made of any polymer stemming from the polymerization of monomeric units including at least one chemical function of the carboxylic acid type. Such monomers are for example acrylic acid, maleic acid, or any ethylenically unsaturated monomer including at least one carboxylic acid function.

Among the examples of a polymer of the anionic type suitable for applying the invention, mention may be made of co-polymers of acrylic acid or of maleic acid or of other monomers, such as acrylamide, alkyl acrylates, $C_5$-$C_8$ alkyl acrylates, $C_{10}$-$C_{30}$ alkyl acrylates, $C_{12}$-$C_{22}$ alkyl methacrylates, methoxypolyethyleneglycol methacrylates, hydroxyester acrylates.

Within the scope of the present description, by «polymer of the cationic type» or «cationic polymer» is meant a polymer including chemical functions of the cationic type. It may also be referred to as a cationic polyelectrolyte.

By «chemical function of the cationic type», is meant a chemical function B capable of catering a proton for obtaining a function BH$^+$. Depending on the conditions of the medium in which it is found, the polymer of the cationic type therefore includes chemical functions in the form of B, or else in the form of BH$^+$, its conjugate acid.

As an example of chemical functions of the cationic type, mention may be made of primary, secondary or tertiary amine functions, optionally present in the form of ammonium cations.

These functions may be comprised within the main chain of the cationic polymers or else borne by said chain or else borne by side chains.

As an example of polymer of the cationic type, mention may be made of any polymer stemming from the polymerisation of monomeric units including at least one chemical function of the primary, secondary or tertiary amine type. Such monomers are for example monomers including aziridine functions, or any ethylenically unsaturated monomer including at least one primary, secondary, or tertiary amine function.

Among the examples of polymers of the cationic type suitable for applying the invention, mention may be made of silicone polymers modified with primary, secondary or tertiary amine functions, such as amodimethicone, derived from a silicone polymer (polydimethylsiloxane, also called dimethicone):

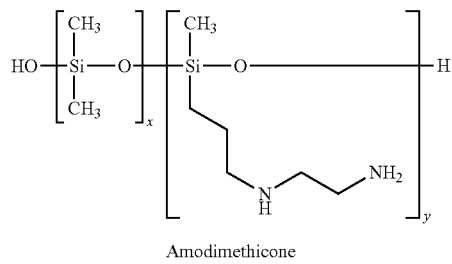

Amodimethicone

Mention may also be made of derivatives of amodimethicone, such as for example copolymers of the amodimethicone, aminopropyl dimethicone, and more generally silicone polymers including amine functions.

Mention may be made of the copolymer of bis-isobutyl PEG-14/amodimethicone and bis-hydroxy/methoxy amodimethicone.

Mention may also be made of polymers of the polysaccharide type comprising amine functions, such as chitosan.

Mention may also be made of polymers of the polypeptide type comprising amine functions such as polylysine.

Mention may also be made of polymers of the polyethyleneimine type comprising amine functions, such as linear or branched polyethyleneimine.

Preferably, the biopolymer R1, and optionally the second reagent R2 when it is present, is in the form of a latex of polymers.

Within the scope of the present invention, by «latex» is meant a stable aqueous dispersion of particles of polymers, generally with a size comprised between 100 nm and 10 μm, preferably between 100 nm and 1 μm, or further between 1 μm and 10 μm.

Natural latex dispersions are commercially available and may be diluted before use in order to reduce their mass fraction of particles of polymers. Generally, within the scope of the present invention, natural latex dispersions are used with a mass fraction comprised from 10% to 60%, preferably from 20% to 40%.

A polymer latex composition may be stiffened by migration through the gelled envelope, of calcium ions contained in the stiffening bath.

In the case of a natural latex, the latter is transformed into rubber during the stiffening step.

The intermediate composition, comprising the biopolymer R1, may further comprise a charging agent, notably when the biopolymer R1 is in the form of a polymer latex.

This filler agent allows reinforcement of the stiffness and the strength of the stiffened intermediate envelope.

As suitable filler agents, mention may be made of silica, carbon black, and generally any inorganic compound in the form of colloidal particles.

Step for Dissolving the Gelled External Envelope

During the method according to the invention, when the capsule comprises an intermediate envelope, the method further comprises a step for dissolving the gelled external envelope.

The depolymerisation step has the purpose of suppressing the gelled external envelope without altering the structure of the stiffened intermediate envelope.

This step may be carried out with any method for depolymerising the hydrogel formed during the gelling step. In the case of a gelled external envelope of alginate, depolymerisation may be carried out by immersion in a depolymerisation solution, such as for example, a sodium citrate solution concentrated to a mass content of a minimum of 5%, typically 10%, or else a saline phosphate buffer solution (further called a PBS buffer).

Mention may further be made of solutions of tartrate ions, of phytic acid or EDTA, any solution of so called chelating species for divalent cations, or further solutions of polymers of acrylic acid of the carbomer, carbopol, polyacrylamide or polyacrylate type.

Generally, the stiffened intermediate envelope is not altered by the step for depolymerisation of the gelled external envelope.

The Capsule According to the Invention

The object of the present invention is also a capsule comprising a liquid core, and at least one external envelope totally encapsulating the liquid core at its periphery, said external envelope being able to retain the liquid core when the capsule is immersed in a gas and comprising at least one gelled polyelectrolyte and/or a stiffened biopolymer, said capsule comprising at least one eukaryotic cell, preferably of a mammal.

By «at least one eukaryotic cell» is meant an isolated cell or a group of cells notably a tissue. These may be differentiated or non-differentiated cells, immortalised cells or tumoral cells. Also, these cells may be adherent or non-adherent. These cells may be cells stemming from any organ or any tissue for example, hepatic tissue, mammary tissue, muscle tissue or skin, more generally co-cultures of tissues such as for example epithelial tissues with their underlying supporting connective tissue, for example the dermis and the epidermis, the intestinal or bronchial mucosa.

Preferentially, the eukaryotic cells are cells of «mammals» are typically cells from any animal notably human cells or stemming from animals widely used as study models such as for example, rabbits, pigs, guinea pigs, mice or the cavy.

The capsules according to the invention have an average diameter from 100 to 1000 μm, preferentially from 200 to 900 μm, 300 to 850 μm, 400 to 800 μm, 450 to 700 μm.

The capsules according to the invention may comprise all the characteristics mentioned earlier during the discussion of their method for obtaining them according to the invention notably in combination with the following features.

The liquid core generally consists of an internal composition generally liquid or slightly viscous, which may be aqueous. The internal composition may also be a dispersion of drops of water in an oily phase, or else a dispersion of oil drops in an aqueous phase, or any type of multiple emulsion of the water/oil/water or oil/water/oil type.

The liquid core may optionally comprise solid particles in suspension, such as metal nanoparticles, mineral particles or composite particles for example. Advantageously, when they are present, the size of said particle is comprised from 10 nm to 10 μm.

The liquid core generally comprises one or several active agents, selected from cosmetic, pharmaceutical, edible or lubricant agents, which may either be hydrophilic or hydrophobic.

In an alternative, the liquid core also comprises a cosmetic active ingredient such as sodium hyaluronate or other moistening/repairing molecules, vitamins, enzymes, anti-wrinkle active ingredients, anti-age agents, protective/anti-radical agents, antioxidants, smoothing agents, softeners, anti-irritation agents, tensing/smoothing agents, emollients, slimming agents, anti-sponginess, firming agents, sheathing agents, draining agents, anti-inflammatories, depigmentation agents, bleaches, self-tanners, exfoliants, stimulating cell renewal or stimulating skin microcirculation, UV absorbants or filtering agents, anti-dandruff agents.

In another alternative, the liquid core comprises an active ingredient advantageously selected from anticoagulants, anti-thrombogenics, anti-mitotic agents, anti-proliferation agents, anti-adhesion agents, anti-migration agents, cell adhesion promoters, growth factors, anti-parasite molecules, anti-inflammatories, angiogenic agents, inhibitors of angiogenesis, vitamins, hormones, proteins, antifungal agents, antimicrobial molecules, antiseptics or antibiotics.

The liquid core may also comprise excipients, such as thickeners or rheological modifiers. These thickeners are for example polymers, cross-polymers, micro-gels, gums or proteins, including polysaccharides, celluloses, polyosides, polymers and co-polymers based on silicone, colloidal particles (silica, clays, latex . . . ).

Alternatively, the liquid core contains reactive agents such as proteins, polysaccharides, fatty acids or their mixture synthesized with eukaryotic cells or intended to form a bioreactor or growing or mature tissues notably for implants.

Preferentially, the pH of the liquid core is between 7.2 and 7.4.

The external envelope is formed with an external aqueous or oily composition and comprise at least one polyelectrolyte which is different from the biopolymer of the intermediate envelope, and at least one surfactant.

According to the invention, the polyelectrolyte of the external envelope is selected from polysaccharides, synthetic polyelectrolytes based on acrylates (sodium, lithium, potassium or ammonium polyacrylate, or polyacrylamide), or synthetic polyelectrolytes based on sulfonates (sodium polystyrene sulfonate), alkaline alginates (such as sodium alginate or potassium alginate), gellans, pectins or their mixture.

The external envelope preferably comprises a reduced amount of surfactant.

The mass percentage of surfactants comprised in the external envelope is generally less than or equal to 0.5%, preferably less than or equal to 0.2%, 0.1% or 0.05% and preferentially less than or equal to 0.025%, 0.03% or 0.01%, based on the mass of the external envelope.

Within the scope of the present description, by «surfactant» is meant an amphiphilic molecule having two portions of different polarity, one being lipophilic and apolar, the other one being hydrophilic and polar. A surfactant may be of the ionic type (cationic or anionic), zwitterionic or non-ionic type. Mention may for example be made of sodium dodecylsulfate (SDS), sodium lauryl ether sulfate (SLES), trimethyldecylammonium, glycocholic acid, taurocholic acid, lecithins, alkylpolyglucosides (APG) or diglycerol esters.

The intermediate envelope when it is present, comprises at least one biopolymer selected from proteins notably of the extracellular matrix, proteoglycans, glycosaminoglycans, polysaccharides and their non-hydrolysed or partly hydrolysed form. Preferentially, the biopolymer is selected from collagen, gelatin, laminin, entractin, at least GAG such as heparane sulfate or their mixture. Typically, the intermediate envelope comprise a mixture of biopolymers such as Geltrex™ or Matrigel™.

Advantageously, the collagen is of the type 1, 2, 3 or 4. It may be non-hydrolysed or partly hydrolysed (chemical or enzymatic hydrolysis).

Preferentially, the intermediate envelope is formed with a mixture of a biopolymer and of a polyelectrolyte.

The biopolymer solution/polyelectrolyte solution volume ratio is greater than 75/25, preferably from 75/25 to 99.9/0.1; 80/20 to 90/10; 70/30 to 80/20; 65/35 to 75/25. For example, the intermediate envelope is a mixture of collagen, preferentially collagen and a polyelectrolyte such as an alginate.

The mass collagen/alginate ratio is greater than 0.6, preferably from 0.6 to 3; 0.8 to 1.8; 0.7 to 1.7; 0.8 to 1.

The inventors have shown that the amount of biopolymer gives the possibility of changing the characteristics of the capsule. Thus, not much polymer does not allow cell adhesion of the adhering eukaryotic cells present in the liquid core, or allows adhesion but reduced cell proliferation is observed. In the case of tumoral cells or non-adhering cells present in the liquid core, the absence of adhesion on the internal face of the intermediate envelope generates the formation of spheroids or a suspension of cells in the liquid core.

In the presence of a biopolymer with a homogenous distribution in the intermediate envelope, cell adhesion is observed, good cell proliferation and a tissue cell organization. For example, in the case of epithelial skin cells for example, the adhesion of the cells to the surface of the intermediate envelope is observed and the formation of a pluristratified epithelium. In the case of dermis cells like fibroblasts, present within the intermediate envelope, a homogenous and disseminated layer structure is observed which is naturally found in the dermis. This is for example observed, when the intermediate envelope has a collagen/alginate mass ratio of more than 0.6.

The intermediate envelope comprises at least one polyol. Typically, the polyol is selected from a monosaccharide, a disaccharide, a polyol polymer and their mixture. Preferentially, the polyol is a monosaccharide selected from glycerol, erythritol, xylitol, arabitol, ribitol, sorbitol, dulcitol, mannitol, volemitol and their mixture. Advantageously, the polyol is a disaccharide selected from maltitol, isomaltitol, lactitol and their mixture. Preferentially, the polyol is sorbitol.

The intermediate envelope is particularly advantageous in that it gives the possibility of compartmenting the capsules and of providing a favourable surface for cell adhesion as well as an adhesional compartment favourable for cell survival, independent of the core of the capsule.

Within the scope of the present invention, the liquid core and/or the intermediate envelope and/or the external envelope comprises at least one nutritive agent. The nutritive agent may be an essential amino acid (arginine, histidine, isoleucine, leucine, lysine, methionine, phenylalanine, threonine, tryptophan, valine, glutamine, cysteine, tyrosine) or a mixture of essential amino acids of mineral salts (notably NaCl, KC, $CaCl_2$, $MgCl_2$, $NaH_2PO_4$ or their mixture), sugars such as sodium pyruvate and/or vitamins. The nutritive agent may be serum (such as foetal calf serum), cell growth factors (EGF, FGF, PDGF), differentiation factors (for example fibronectin), enzymatic inhibitors (inhibitors of trypsin for example, such as alpha-1 antitrypsin) and/or antibiotics (Penicillin G, Streptomycin, Amphotericin B).

Advantageously, the nutritive agent is introduced into a buffer such as a phosphate buffer (PBS phosphate-buffered saline) or a cell culture medium for example RPMI (Roswell Park Memorial Institute medium), MEM (Minimum Essential Medium Eagle), or DMEM (Dulbecco/Vogt modified Eagle's minimal essential medium).

Preferentially the pH of the liquid core and of the intermediate envelope and/or of the external envelope is between 7.2 and 7.4.

A capsule may contain 1 to $10^{12}$ cells, preferentially, 10 to $10^{10}$, 20 to $10^9$, 30 to $10^8$, 40 to $10^7$, 50 to $10^6$, 100 to $10^5$, 150 to $10^4$, 200 to $10^3$ eukaryotic mammalian cells.

Gelled and Stiffened Capsules

According to a first embodiment (see FIG. 1), a capsule 10 according to the invention further comprises a gelled external envelope 40 totally encapsulating at its periphery the stiffened envelope 30.

According to a first alternative, the gelled and stiffened capsules comprise eukaryotic cells 70 only in the liquid core 20 (FIG. 5A). According to other alternatives, the gelled and stiffened capsules comprise eukaryotic cells 70 in the liquid core 20 and in the intermediate envelope 30 when said capsule only comprises an intermediate envelope or in its two intermediate envelopes 30 and 90 when said capsule 80 comprises two of them (FIGS. 5B and 5D). According to a third alternative, the gelled and stiffened capsules comprise eukaryotic cells 70 in the liquid core 20, in the intermediate envelope and in the external envelope 40 when said external envelope contains at least one biopolymer (FIG. 5C).

Such capsules correspond to the gelled and stiffened capsules defined above, and are typically obtained by producing multi-component drops by co-extrusion with separate conveyance in an envelope with multiple flows. In the case of a triple envelope, the three flows are: a first flow consisting of the internal composition, a second flow consisting of the intermediate composition and a third flow consisting of the external composition. The multi-component drops are then subject to a gelling step and then a stiffening step according to the method of the invention.

Preferably, the gelled external envelope of the capsules according to the invention have a thickness comprised from 10 μm to 500 μm, preferably from 20 μm to 200 μm, and advantageously from 45 μm to 150 μm, more preferentially, 50 μm to 100 μm.

By the thinness of the thickness of the gelled external envelope it is generally possible to make this external envelope transparent.

The capsules according to the invention generally have a volume ratio between the core and the whole of the intermediate and external envelopes of more than 2, and preferably less than 50.

According to a particular embodiment, the capsules according to the invention generally have a volume ratio between the core and the whole of the intermediate and external envelopes comprised between 5 and 10.

The presence of a surfactant in the external composition gives the possibility of improving the formation and the gelling of multi-component drops according to the method as described earlier. Nevertheless, in order to improve cell survival, the mass percentage of surfactant comprising a capsule according to the invention is preferentially less than or equal to 0.050%, preferably less than or equal to 0.025% and preferentially less than or equal to 0.010%, or even less than or equal to 0.005%, preferentially less than or equal to 0.001%, or even less than or equal to 0.0005% based on the total mass of the capsule. Preferentially, the mass percentage of surfactant comprised in the external envelope, is preferentially less than or equal to 0.050%, preferably less than or equal to 0.025% and preferentially less than or equal to 0.010%, or even less than or equal to 0.005%, based on the total mass of the external envelope.

Stiffened Capsules

According to another embodiment (see FIG. 2A), a capsule 50 according to the invention comprises a liquid core 20 and a stiffened external envelope 30 totally encapsulating at its periphery the liquid core 20.

According to a first alternative, the stiffened capsules 50 comprise eukaryotic cells 70 only in the liquid core 20 (FIG. 3A). According to a second alternative, the stiffened capsules comprise eukaryotic cells 70 in the liquid core 20 and in the stiffened external envelope 30 (FIG. 3B).

Such capsules correspond to stiffened capsules, without any gelled envelope. These capsules are typically obtained by producing multi-component drops by co-extrusion with separate conveyance in a triple envelope of three flows: a first flow consisting of the internal composition, a second flow consisting of the intermediate composition and a third flow consisting of the external composition. The multi-component drops are then subject to a gelling, stiffening step and finally to a depolymerisation step according to the method of the invention.

After removal of the gelled external envelope, the intermediate stiffened envelope becomes the stiffened external envelope of the stiffened capsules. These capsules then benefit from surface properties of the stiffened envelope, which may be of the hydrophilic type or of the lipophilic type.

The stiffened envelope is intended to provide new surface properties to the capsules of the core-envelope type described earlier, by getting rid of the limit set by the nature of the external envelope, which was up till now essentially of the hydrogel type (cf. notably WO 2010/063937).

Given the diversity in the selection of the materials making up the stiffened intermediate envelope, the thereby obtained capsules may have any type of functionality at their surface.

It is therefore possible to concentrate the preparation of capsules having surface properties adapted to diverse fields, such as for example in biotechnology applications.

It is therefore also possible to contemplate the obtaining of highly superior encapsulation performances, without constraints on the nature of the solution to be encapsulated. This is particularly sought in certain applications for which there are no satisfactory existing solutions.

As an example of interesting surface properties which were not available with the capsules known up till now including a gelled envelope, and which are now accessible with the stiffened capsules according to the invention, mention may be made of sealing properties, stiffness or on the contrary elasticity properties, or else having biomimetism properties.

In particular, when the stiffened envelope is based on latex, stiffened capsules are obtained including an external envelope with a significant seal, even towards water.

In particular, when the stiffened envelope comprises at least one biopolymer which is selected from proteins of the extracellular matrix, proteoglycans, glycosaminoglycans, polysaccharides and their non-hydrolysed or partly hydrolysed form, the stiffened envelope allows cell adhesion. Preferentially, the biopolymer is selected from collagen, gelatin, laminin, entractin, at least one GAG such as heparane sulfate or their mixture. Typically, the biopolymer is a mixture such as Geltrex™, Matrigel™ or collagen. Thus, with the invention it is possible to obtain stiffened capsules including an envelope for which the internal surface is biomimetic and favourable for the growth of plant, animal or human cells.

Generally, a stiffened envelope obtained for example by coacervation of polymers is stiffer, more impervious and less permeable than a gelled envelope obtained by gelling.

It is therefore understood that the stiffened capsules of the invention have increased sealing properties as compared with the simply gelled capsules of the prior art.

It is also possible to functionalise the surface of the stiffened envelope in order to provide the capsules with the desired properties, such as hydrophilicity, lipophilicity, electric changed properties.

It may notably be contemplated to encapsulate, as an active agent, cosmetic, pharmaceutical, edible, compounds, lubricants, proteins, reagents intended to form a bioreactor or for cells intended to divide.

It is also possible to contemplate encapsulation of the cells for cell cultivation or for implants or cells intended to form tissues. In this case, the stiffened external envelope of the capsules is advantageously permeable to the nutrients of the outer medium so that the cells develop efficiently.

It is also possible to contemplate the encapsulation of proteins, polysaccharides or nucleic acids or the encapsulation of cells so that they produce these proteins, polysaccharides or nucleic acids. In this case, the stiffened external envelope of the capsules, typically based on latex is advantageously permeable only to water. The desalting of the core is then typically caused by bursting of the capsule by an osmotic shock when the capsule is in contact with water.

Preferably, the stiffened envelope of the capsules according to the invention have a thickness comprised from 10 µm to 1000 µm, preferably from 1 µm to 1000 µm, and advantageously from 20 µm to 500 µm.

The capsules according to the invention generally have a volume ratio between the core and the stiffened envelope of more than 2, and preferably less than 50.

According to a particular embodiment, the capsules according to the invention generally have a volume ratio between the core and the stiffened envelope comprised between 5 and 10.

The capsules according to the invention, provided with or without any gelled external envelope, generally have an average size comprised from 100 µm to 6 mm, preferably from 100 µm to 500 µm.

For a use of the capsules in a cell culture or in biology generally, an advantageous size of the capsules is typically located from 100 µm to 1000 µm, preferentially from 250 to 700 µm.

Gelled Capsules

According to another embodiment (see FIG. 2B), a capsule 60 according to the invention comprises a liquid core 20 and a gelled external envelope 40 totally encapsulating at its periphery the liquid core 20.

According to a first alternative, the gelled capsules 60 comprise eukaryotic cells 70 only in the liquid core 20 (FIG. 4A). According to a second alternative, the gelled capsules 60 comprise eukaryotic cells 70 in the liquid core 20 and in the gelled external envelope 40 when said gelled external envelope comprises at least one biopolymer (FIG. 4B).

These capsules are typically obtained by producing multi-component drops by co-extrusion with separate conveyance in a double envelope by co-extrusion of two compositions.

In this case, the double envelope conveys two flows: a first flow consisting of the internal composition, a second flow consisting of the external composition and then according to the method of the invention, the obtained drops are subject to a gelling step.

Three-Dimensional Culture Model Capsules

In order to set into place a three-dimensional culture model, the capsules used may be gelled capsules, stiffened gelled capsules or stiffened capsules. Preferentially, these capsules may contain eukaryotic mammalian cells in the liquid core and/or in the intermediate envelope and/or in the external envelope, when it contains a biopolymer.

Preferably, the external envelope comprises an alginate, the rigid envelope comprises collagen or a mixture of collagen, gelatin, laminin, entractin and heparane sulfate. A polyol such as sorbitol may be added into the composition of the intermediate envelope.

The eukaryotic cells are preferentially murine or human cells notably, these may be tumoral cells or cells from a specific tissue such as blood, breast, liver, dermis or epidermis notably.

As an illustration, in order to obtain skin models, several alternatives may be applied notably from a capsule comprising an intermediate envelope, an external envelope and a liquid core.

According to a first alternative, the capsules contain in the liquid core keratinocytes. These capsules are particularly advantageous in that they are a good model of the epidermis and notably allow screening of cosmetic active ingredients intended for the epidermis.

According to a second alternative, the intermediate envelope comprises fibroblasts and the liquid core does not comprise any cells. In this case, this is an advantageous dermis model which notably allows screening of cosmetic active ingredients intended for the dermis.

According to a particular embodiment of the invention, the liquid core comprises keratinocytes and the intermediate envelope comprises fibroblasts and/or melanocytes. Such a capsule forms a skin model of interest in that it forms a three-dimensional model of the dermo-epidermal junction allowing screening of actives while getting rid of the influence of the extracellular matrix.

It should be noted that the reconstruction of a skin tissue within alginate capsules requires allowing compartmentation of these capsules into two areas corresponding to the two sheaths making up the skin, i.e. the epidermis and the dermis. From a biological point of view, the composition of the intermediate envelope allows survival and growth of fibroblasts which will be disseminated in its interior, thereby regenerating a matrix similar to the dermal matrix. Finally, the composition of the intermediate envelope allows adhesion of the keratinocytes to its surface.

The capsule according to the invention meets the whole of these criteria and allows establishment of an accurate skin model.

The stiff capsules in which the gelled envelope has been depolymerised are of interest for establishing a basal lamina models in order to for example study the interactions between a cell type (epithelial or tumoral cell) with the basal lamina. In this case, the stiff envelope may comprise collagen or a mixture of collagen, gelatin, laminin, entractin and heparane sulfate. Preferably, a polyol such as sorbitol is added into the composition of the envelope. According to this alternative, the investigated cells are comprised in the liquid core. This model notably allows the study of cell migration notably the case of metastasis.

Method for Storing Eukaryotic Cells

In the pharmaceutical industry or in the cosmetic industry, the aforementioned capsules are notably filled with biologically or cosmetically active products. They are notably used for protecting their contents and for controlling the desalting of the product which they contain. The capsules according to the invention are particularly suitable for storing or keeping biological samples notably of eukaryotic cells, preferentially mammalian cells in the form of isolated cells or tissues, for obtaining three-dimensional culture models, for producing or screening with a high flow rate of a notably cosmetic active ingredient.

The present invention therefore relates to a method for storing or keeping eukaryotic cells, preferably mammalian cells notably in the form of isolated cells or tissues comprising a step for preparing a capsule by the method according to the invention and a step for storing said obtained capsules.

The method for preparing capsules gives the possibility of obtaining at least one outer envelope in one piece guaranteeing the hermeticity of the latter and thus good preservation of the liquid core.

The liquid core may optionally comprise a storage agent, such as a buffer (Hepes buffer) or a cryoprotection agent i.e. methyl acetamide, methanol, ethylene glycol, polyvinylpyrrolidone, dimethylsulfoxyde (DMSO) or glycerol. The storage conditions are known one skilled in the art. Thus, capsules containing eukaryotic cells as well as a storage agent may be kept in liquid nitrogen for quite long durations.

Within the scope of the present invention, the liquid core, the intermediate envelope and/or the external envelope comprises at least one nutritive agent.

Preferentially, the pH of the liquid core, of the intermediate envelope and/or of the external envelope is between 7.2 and 7.4.

Use of a Capsule for Ex Vivo Cultivation of Eukaryotic Mammalian Cells and In Vitro Method for Cultivating Eukaryotic Cells The invention further relates to the use of a capsule according to the invention for in vitro cultivation of eukaryotic mammalian cells.

The invention further relates to an in vitro method for cultivating eukaryotic cells comprising the following steps:
 a) cultivating a capsule according to the invention under sufficient conditions for cell growth, and
 b) harvesting said capsule.

The capsules according to the invention allow in vitro or in capsular cultivation of adherent cells such as cells from an organised tissue like skin, the liver, the breasts, or of non-adherent cells such as cells of a non-organised tissue like blood or tumoral cells.

The capsule according to the invention allows cultivation of eukaryotic mammalian cells in suspension and/or as spheroid and/or as a tissue.

The capsules according to the invention may be cultivated under «sufficient conditions for cell growth» which are known to one skilled in the art, such as notably in the presence of a buffer or a basic culture medium adding with at least one nutritive agent as described earlier. The «conditions sufficient for cell growth» notably the conditions and times for incubation may be adapted according to the cell type by one skilled in the art, the capsules may notably be cultivated at 37° C. with 5% $CO_2$.

The cells may be cultivated in a «basic culture medium» suitable for a growth, according to the cell type use, this medium may be a synthetic medium with or without serum, currently available commercially, such as a medium without any serum of the RPMI type, or a medium with serum, IMDM, MEM or DMEM. This medium is added with at least one nutritive agent as defined above. The presence of serum in the culture medium is not mandatory but improves the cultivation results. The basic culture medium may conventionally contain or be added with antibiotics for avoiding contaminations during cell cultivation, and with glutamine.

A suitable basic culture medium for human fibroblasts may for example be a complete DME medium, i.e. a Dulbecco-Vogt modification of Eagle's medium (DMEM; Gibco, Burlington, On, Canada) containing 10% of foetal calf serum (FCS; Hyclone, Logan, Utah, USA), 100 U/ml of Penicillin G (Sigma) and 25 µg/ml of Gentamycin (Schering, Pointe-Claire, Qc, Canada). The capsules are incubated at 37° C. in 8% $CO_2$ and the culture medium may be changed every 2 days.

A medium suitable for keratinocytes is known to one skilled in the art for example, a basic culture medium may be a complete DME medium in the presence of growth factors, notably of amino acids, serum, choleric toxin, insulin, tri-iodo-thyronine and pH buffer solution. In particular, such a culture medium may notably contain at least one mitogenic growth factor for keratinocytes (for example the epidermal growth factor (EGF) and/or keratinocyte growth factor (KGF), in particular KGF), insulin, hydrocortisone and optionally an antibiotic (eg: Gentamycin, Amphotericin B). The capsules are incubated at 37° C. in 5% $CO_2$ and the culture medium may be changed every 2 days.

For the melanocytes, the adapted culture medium will either contain or not phorbol ester and may consist of a basic medium such as DMEM/F12 or MCDB153 added with growth factors specific to melanocytes (such as for example bFGF, FCS, ET-1, ET3, aMSH) and in particular in the medium M2 (Promocell) or in other media such as M254 (Cascades Biologics™). The capsules are incubated at 37° C. in 5% $CO_2$ and the culture medium may be changed every 2 days.

Such capsules may be cultivated for example up to one month at 37° C.

The harvesting of the capsules may be ensured by simply removing the culture medium by filtration or by any other technique for re-enveloping the capsules.

Method for Screening Active Ingredients

The invention also deals with a method for screening active ingredients comprising:
 a) cultivation of a capsule according to the invention in the presence and in the absence of a candidate substance,
 b) detection of a phenotype of interest in the cells of the cultivated capsule in the presence of the candidate substance as compared to the cells of the cultivated capsule in the absence of the candidate substance, and
 c) identification of the substance as a cosmetic active ingredient if a phenotype of interest was detected.

In the present application, by «active ingredient» is meant a molecule which has a therapeutic or cosmetic effect, this is therefore a therapeutic or cosmetic active ingredient. An active ingredient may be free or carried (in a solvent or in a mixture with an excipient), encapsulated (for example in liposomes), or vectorised (for example in nanoparticles with screening ligands at the surface). For example, this may be any molecule having therapeutic properties entering the composition of a drug. Mention may for example be made of anticoagulants, anti-thrombogenics, anti-mitotic agents, anti-proliferation agents, anti-adhesion agents or antibiotics. This list is not exhaustive and extends to any therapeutic active ingredient known to one skilled in the art. This may be also any molecule entering the composition of a cosmetic preparation which ensures the efficiency of the product (as opposed to the other ingredients of the composition such as the excipients or other additives (adjuvants, preservatives) which ensure a different function). Thus, an active ingredient may be any molecule ensuring the cosmetic effect of the cosmetic product such as hygiene products, care products, hair care products in order to mention only a few of them. Cosmetics are hygiene and beauty products. A cosmetic is a substance or a preparation intended to be put into contact with diverse surface portions of the human body, with the view, exclusively or mainly of cleaning, protecting, perfuming them, maintaining the human body in good condition, modifying its aspect or correcting the smell thereof. Thus, by «cosmetic effect», is meant in the present description, the aforementioned hygiene or beauty effect which the product is intended to accomplish and is designed for this. As cosmetic active ingredients, mention may be for example made of fruit acids (exfoliants), retinol or vitamin A (antioxidant), certain essential oils, aloe vera, algae extracts, and amino acids. This list is not exhaustive and extends to any cosmetic active ingredient known to one skilled in the art.

The «candidate substance» according to the invention is a molecule of natural or synthetic origin for which the intention is to test the therapeutic or cosmetic effect. This molecule may be a small size or large size chemical molecule such as a polymer, a biological molecule such as a peptide, a protein, a saccharide or a polysaccharide, a nucleic acid or a fatty acid.

Said candidate substance may be added to the buffer or to the culture medium in which the capsules are incubated.

By «phenotype of interest» is meant any modification of a biological characteristic of the cell, such a modification may for example be expressed by the stopping of cell proliferation, cell death, the expression of cell markers, or a loss of intercellular adhesion or detachment of the cells from the walls of the capsule.

The phenotype of interest may be detected by direct observation notably with specific fluorescent marking such as direct fluorescence (GFP) or immunofluorescence, or by any other genomic or proteomic technique known to one skilled in the art.

The screening method according to the invention is advantageous in that it allows a high flow rate screening in physiologically relevant 3D environments, it also allows detection, selection, and re-enveloping of the analysed cells which may be accomplished with automated means. Conversely, by the encapsulation of an individual cell and then a cultivation, the method according to the invention allows simultaneous exposure of a very large number of cell colonies to strictly identical experimental conditions.

Although having distinct meanings, the terms of «comprising», «containing», «including» and «consisting in» have been used interchangeably in the description of the invention, and may be replaced with each other.

The invention will be better understood upon reading which follows, only given as an example, and made with reference to the appended drawings, wherein.

Figure 5:
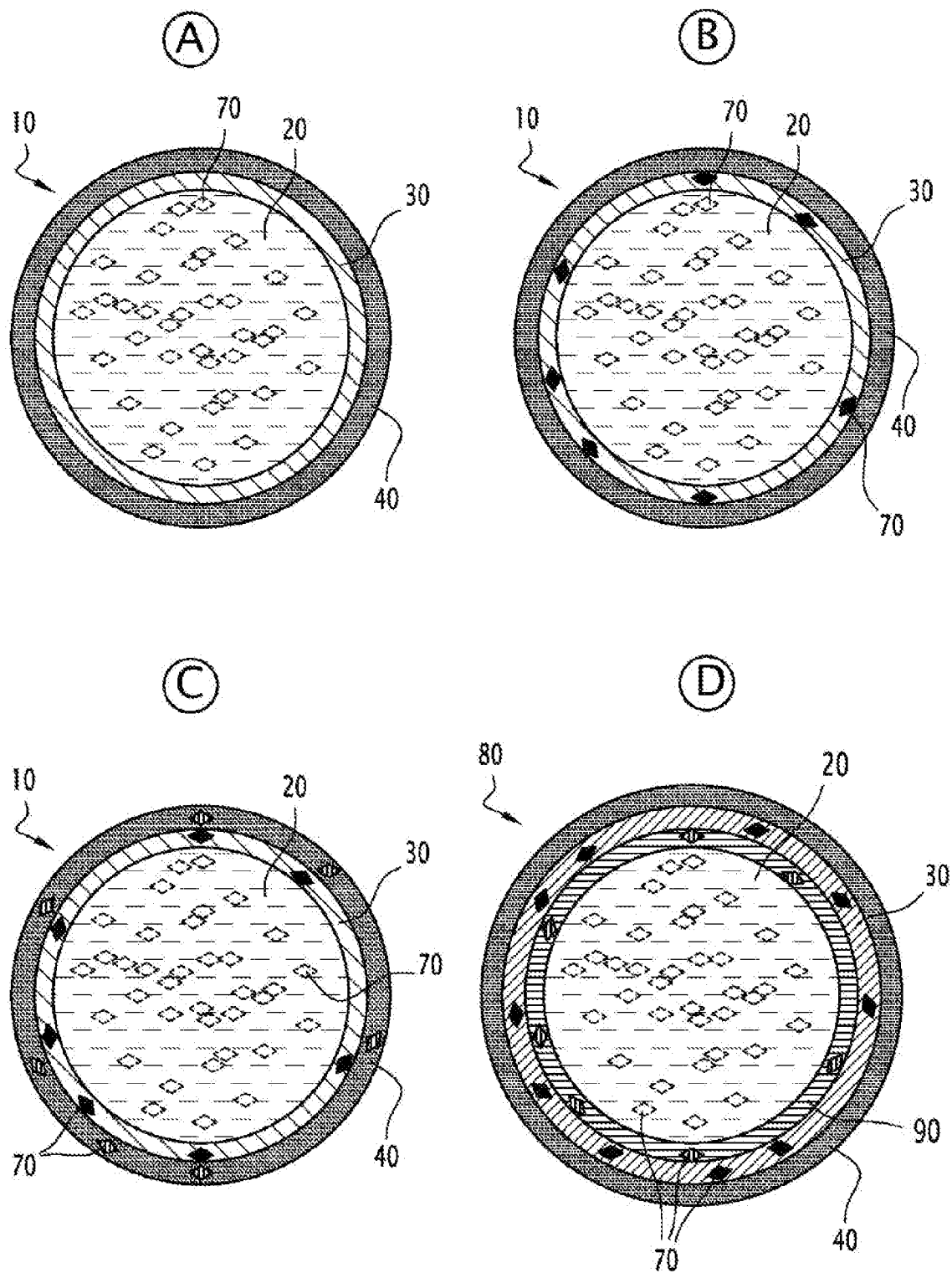

FIG. 5 is a large scale view in a section along a middle vertical plane of a gelled and stiffened capsule according to the invention comprising a liquid core, an external envelope and at least one intermediate envelope. In FIG. 5A, the gelled and stiffened capsule comprises eukaryotic cells in the liquid core. In FIG. 5B, the gelled and stiffened capsule comprises eukaryotic cells in the liquid core and in the intermediate envelope. In FIG. 5C, the gelled and stiffened capsule comprises eukaryotic cells in the liquid core, in the intermediate envelope and in the external envelope. In FIG. 5D, the gelled and stiffened capsule comprises two intermediate envelopes, the liquid core as well as the two intermediate envelopes comprising eukaryotic cells.

Figure 6:
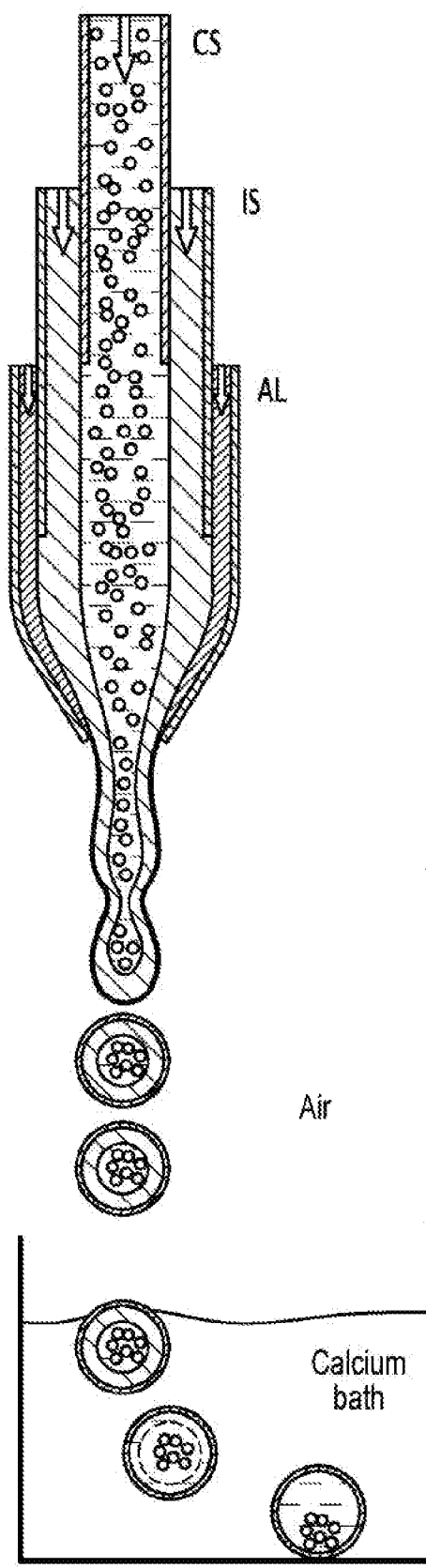

FIG. 6 deals with the design and the principle for operating the microfluidic device for forming a microcapsule. The microfluidic platform consists of an external fluidic injection system, of a co-extrusion micro-device and of a gelling bath outside the chip (not shown). The enlarged view of the chip shows the 3 way configuration with the cell suspension (CS), the intermediate solution (IS), and the alginate solution (AL) respectively circulating in the most internal, intermediate and the most external capillary. The inlet orifices of the chip are collected to 3 syringes controlled by 2 syringe pumps. The liquid micro-droplets of compound fall into a 100 mm iso-osmotic calcium bath. The gelling of the alginated shell mediated by the calcium sets the structure of the capsule while the internal solutions diffuse and maintain the cells encapsulated. The analysis of the jet at the outlet of the end piece by a high speed camera, shows that at a low flow rate q (total flow rate), formation of droplets of the order of a millimetre is observed. At a high flow rate q, the intact length of the jet is too long as compared with the distance between the end piece and the gelling bath. No formation of droplets is observed when the flow enters into contact with the bath. At an intermediate flow rate q (typically between 50 and 150 ml·h$^{-1}$), dispersion of the jet and formation of drops occurs before impact.

Figure 7:
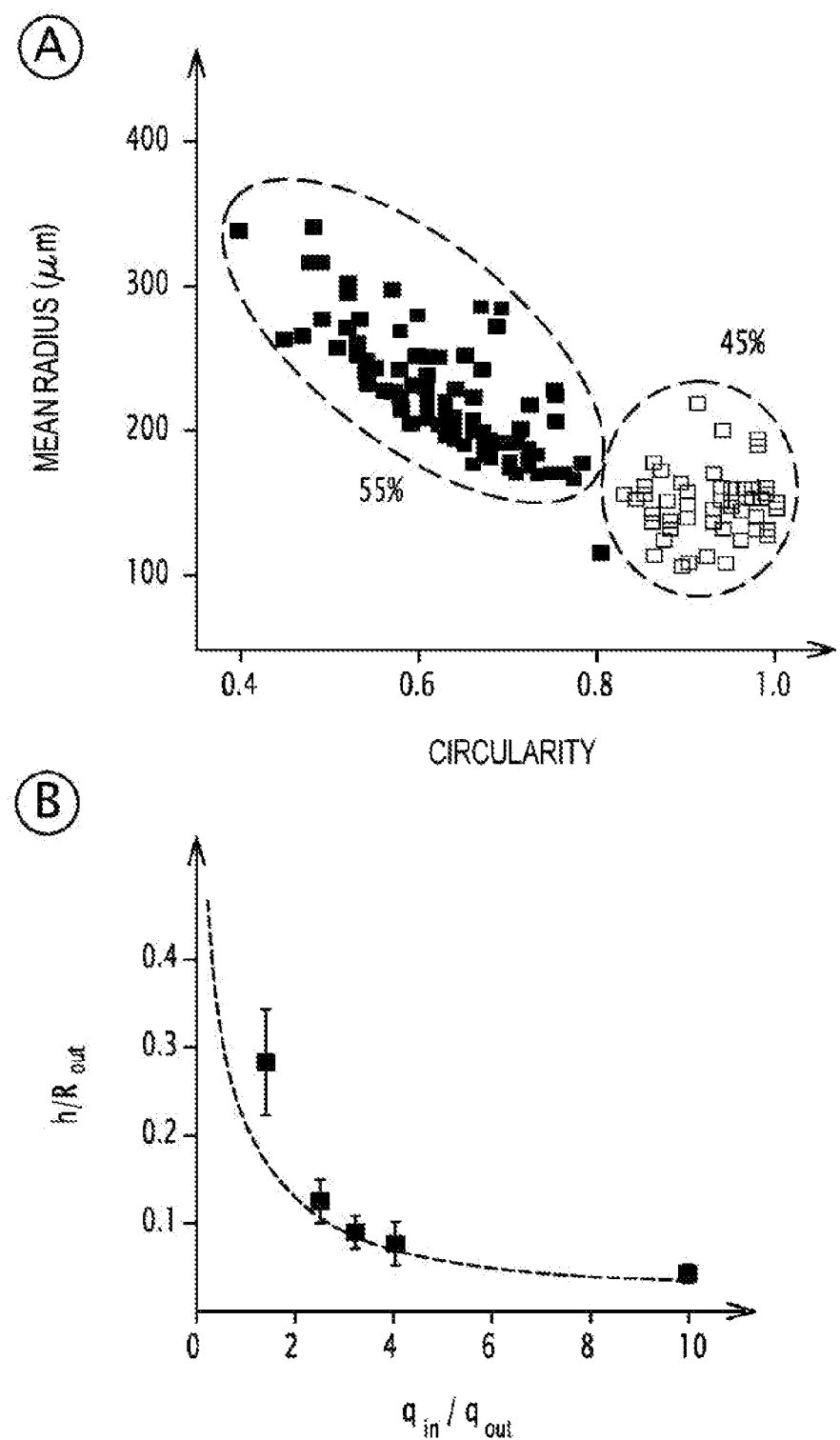

FIG. 7 deals with the morphometric and mechanical characterisation of the microcapsules of alginate. (A) is a typical 2D point plot of the average radius depending on the circularity of capsules (without cells) directly collected from the gelling bath showing the existence of two populations of capsules: the fraction of the small spherical capsules (R~150 µm) (45%) and the fraction of the ellipsoidal or deformed largest capsules (55%) following coalescence of the droplets. (B) is a plot of the aspect ratio of the capsule h/R$_{out}$ versus the ratio between the internal and external flow rates q$_{in}$/q$_{out}$. The black points are the experimental data. The dotted line is the theoretical curve derived from conservation of the volume (see example 5, section Methods).

Figure 8:
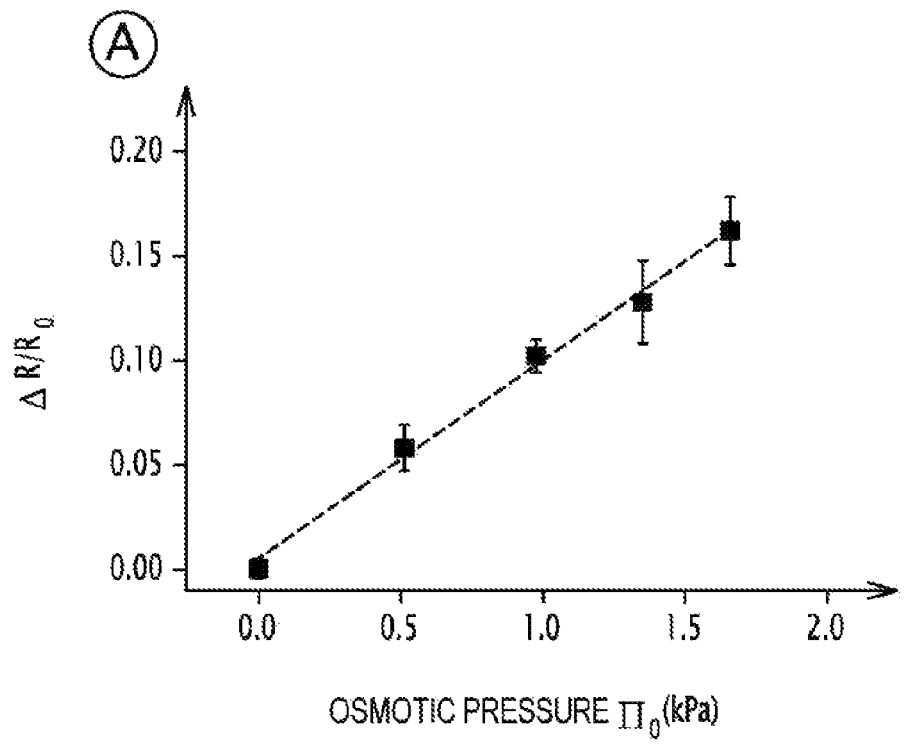
Figure 8:
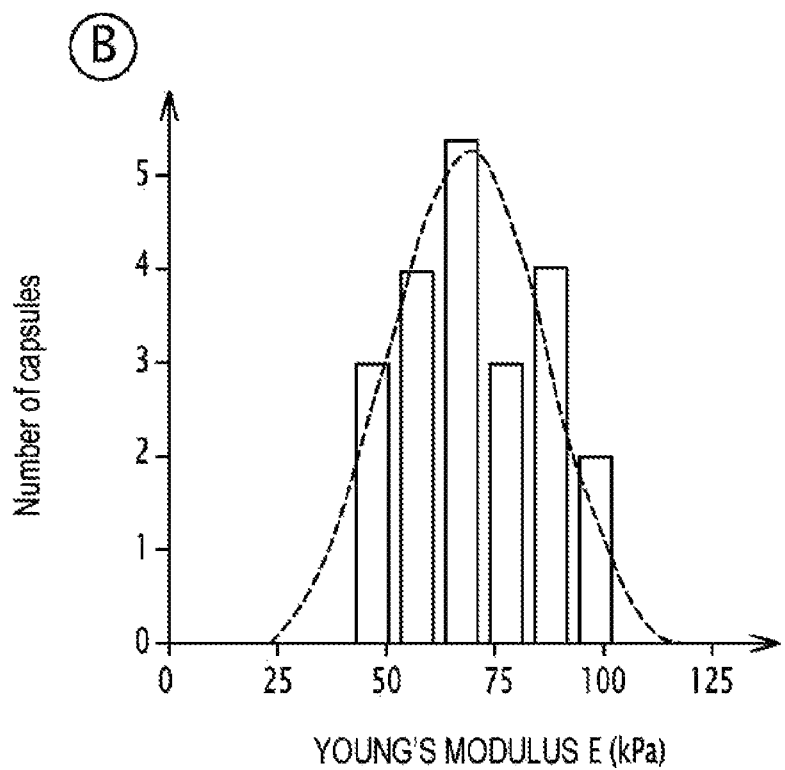

FIG. 8 (A) is the plot of the deformation of the capsule AR/R0 versus the osmotic pressure difference π0. (B) is the Young Modulus E of an alginate gel from an osmotic inflation test. The Young modulus E of the alginate gel is derived from the slope of the dotted line which is adjusted to the data of the plot A. Representative histogram of the distribution of the values of the Young modulus (n=26).

Figure 9:
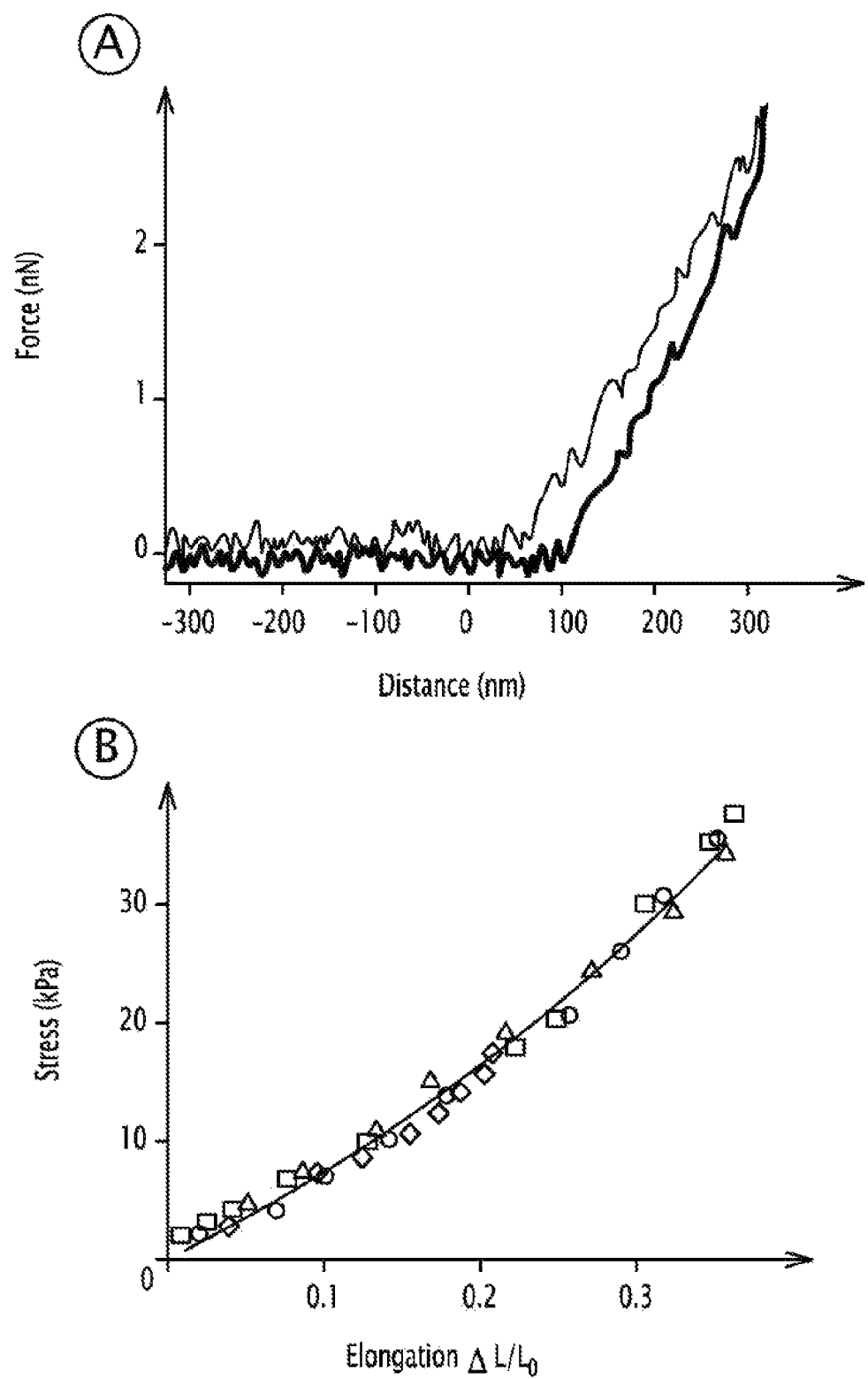

FIG. 9 (A) Micro-indentation of alginate gel capsules by using atomic force microscopy. Typical approach force-displacement curves (thin line, upper curve) and retraction curves (thick line, bottom curve) were obtained on a single capsule. (B) Elongation of macroscopic alginate threads. Stress-elongation plot for 5 different cylinders of alginate gel (length at rest of about 0.2 m, diameter of about 1 mm). The stress is derived from the weight of the calibrated masses by assuming a Poisson ratio of the gel v=½. The line is a polynomial adjustment to the data of the second order generating a dependency on phenomenological constraints of the Young modulus at a significant deformation.

Figure 10:
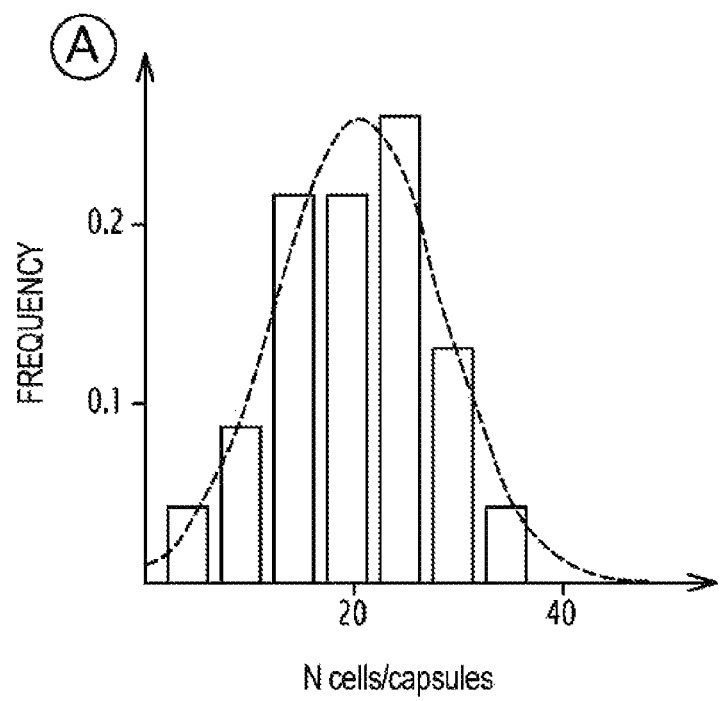
Figure 10:
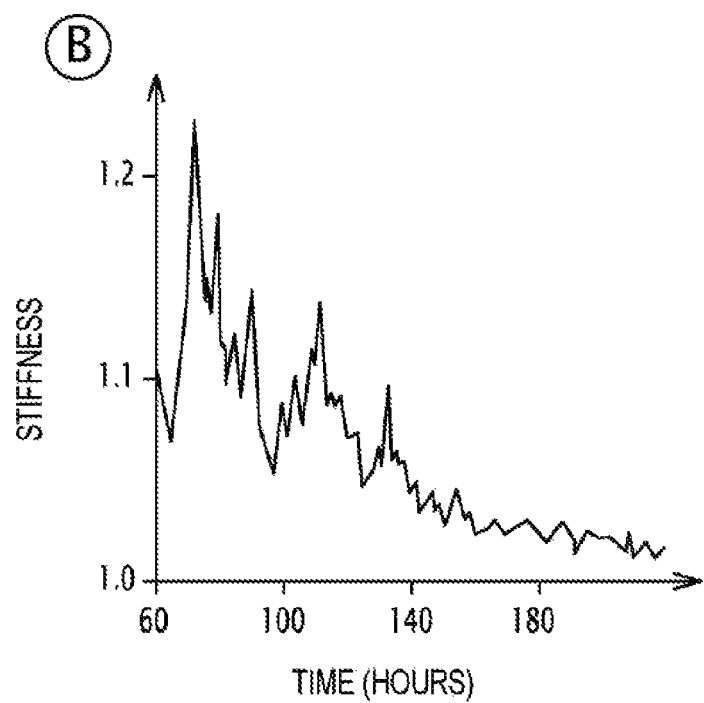

FIG. 10 (A) Distribution of the average number of cells per capsule adjusted with a Gaussian curve. The count of the cells is obtained from phase contrast micrographs of the individual capsules merged with epifluorescence micrographs of encapsulated cells coloured with colouring agents for living/dead cells. (B) Plot of the stiffness of the MCS versus time from measurements obtained by photographs acquired with a phase contrast microscope, from a spheroid of cells CT26 in expansion inside a capsule until confluence. The time t=0 corresponds to encapsulation.

Figure 11:
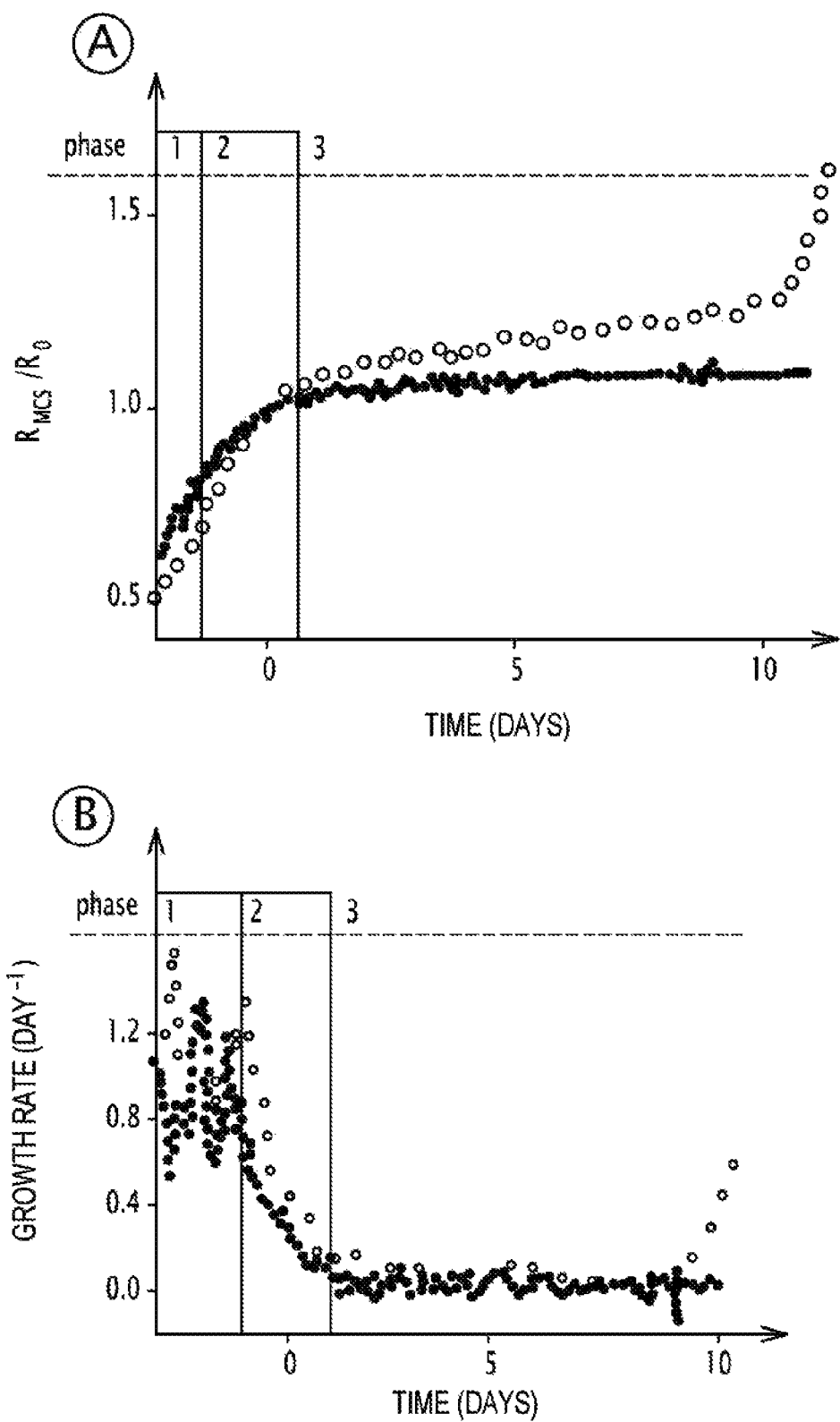
Figure 12:
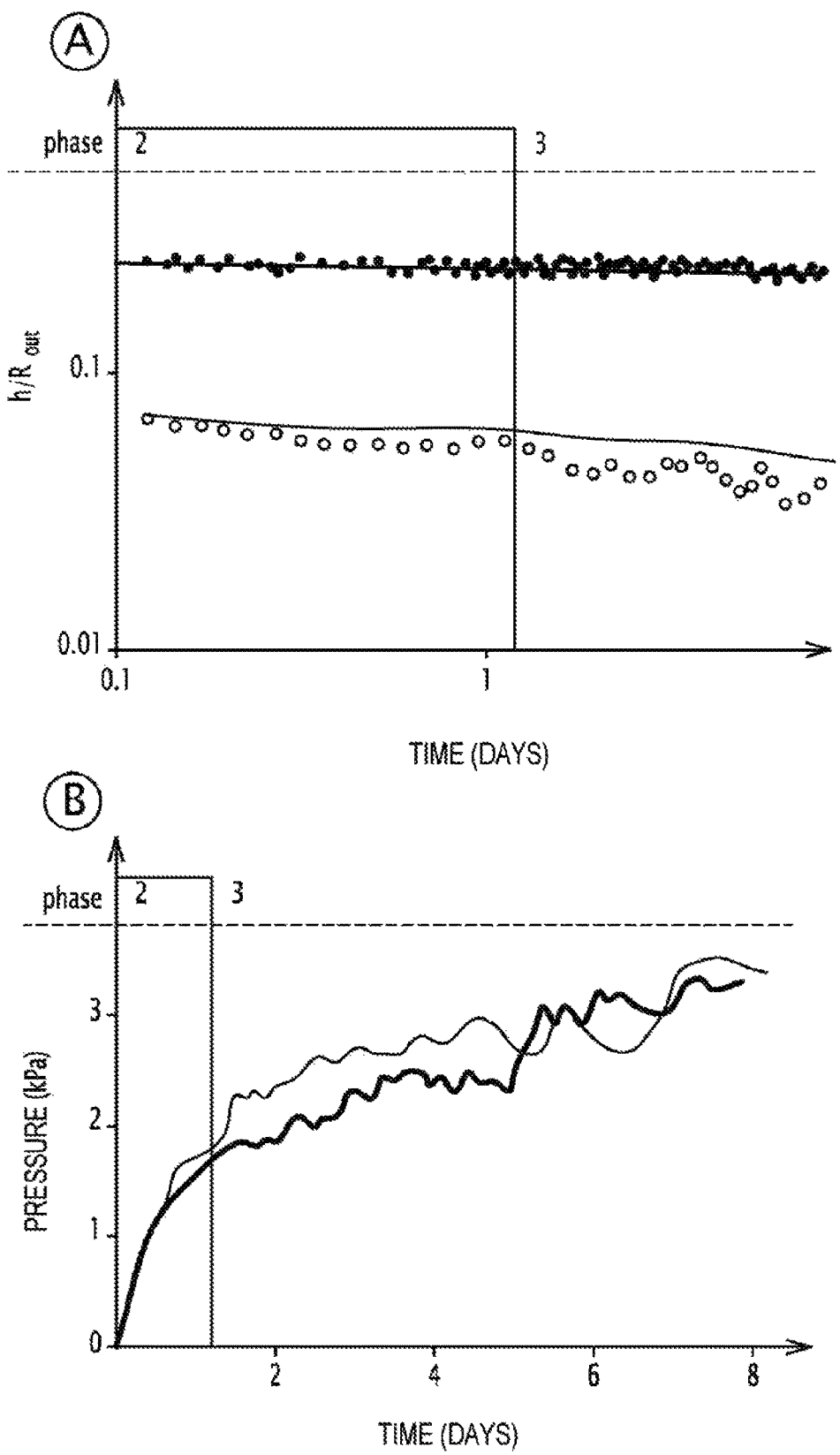

FIGS. 11 and 12 deal with the quantitative analysis of the growth of spheroids and of the deformation of the capsules. Representative time plots show the influence of the stiffness of the capsule (via the thickness of the shell) on the growth and the mechanical characteristics of the MCS. FIG. 11A illustrates the study of the normalised radius of the spheroid R$_{MCS}$ relatively to the internal radius of the non-deformed capsule R$_0$ versus time. FIG. 11B represents the study of the apparent growth rate 3Ṙ$_{MCS}$/R$_{MCS}$ versus time. FIG. 12A represents the study of the aspect ratio $h/R_{out}$ of the capsule versus time. The points are the experimented data. The lines are the theoretical predictions by assuming that the alginate gel is an incompressible material. FIG. 12B represents the study of the pressure exerted by the spheroid on the wall of the capsule versus time. The points with an anti-centre and the thin lines correspond to a thin capsule (h=8 μm). The solid points and the thick black lines correspond to a thick capsule (h=28 μm). The different phases discussed in the text are identified with grey rectangles. Confluence is considered as like the reference time t=0.

Figure 13:
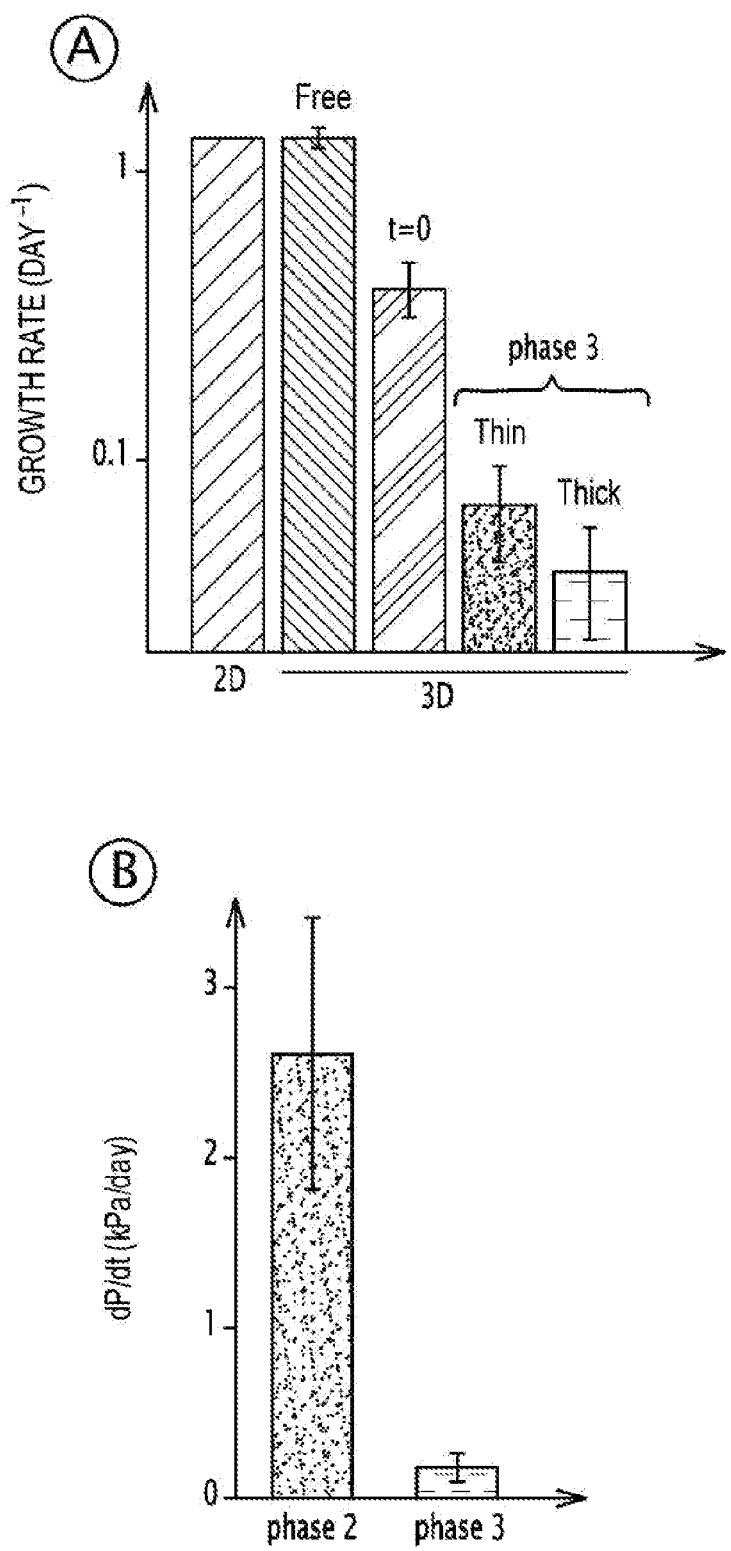

FIG. 13 deals with the statistical analysis (n=23 for the thin capsules and n=17 for the thick capsules). FIG. 13A represents the study of the apparent growth rate of the spheroid according to a logarithmic scale for cell monolayers (2D), spheroid in free expansion (3D, free), spheroids encapsulated to confluence (3D, t=0), and during the last stages (phase 3) for the two shell thicknesses (3D, thin and thick). The pressure rate increases (13B) just after confluence (phase 2) and during the last stages (phase 3). FIG. 13C represents the phase contrast intensity study versus the radial distance relatively to the centre of the MCS and versus time. The bright line is the external wall of the capsule. Scale bars, 20 hours and 50 μm.

Figure 14:
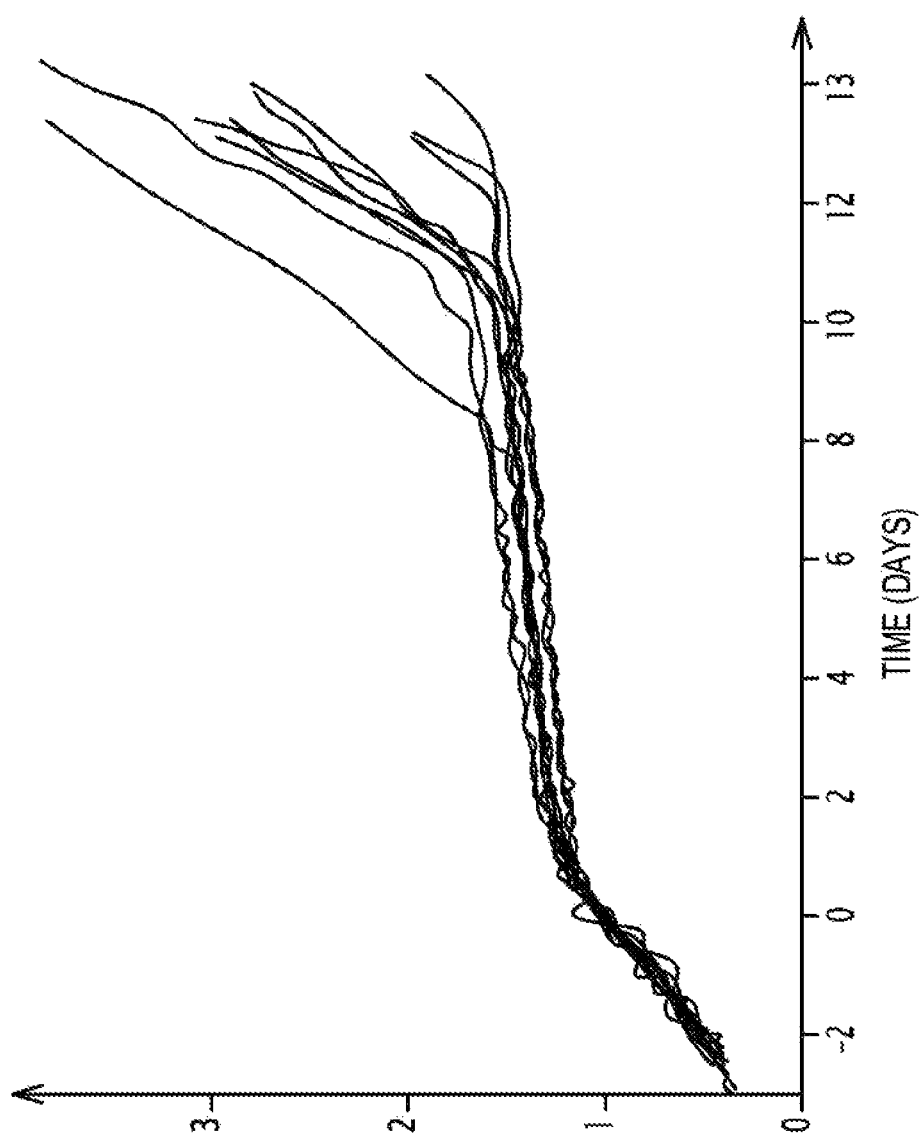

FIG. 14 Growth of spheroids inside the alginate capsules and after bursting of the capsules. Representative plots showing the time dependent change of the radius of the spheroid $R_{MCS}$ normalise relative to the initial internal radius of the capsule $R_0$ for different spheroids CT26 in expansion in thin capsules. The time t=0 is the moment of confluence. The sudden increase in $R_{MCS}$ during the last stages corresponds to the bursting of the capsule. The spheroid freely grows at a rate similar to the one observed during the very early stages following encapsulation.

Figure 15:
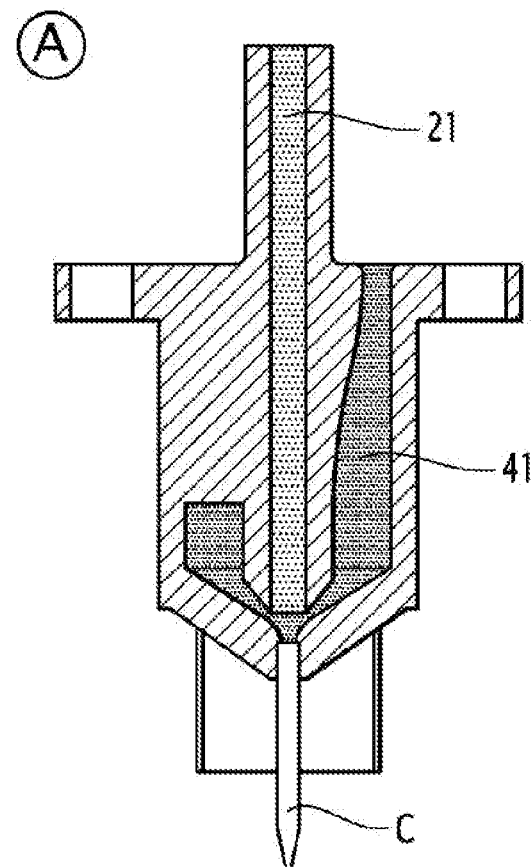
Figure 15:
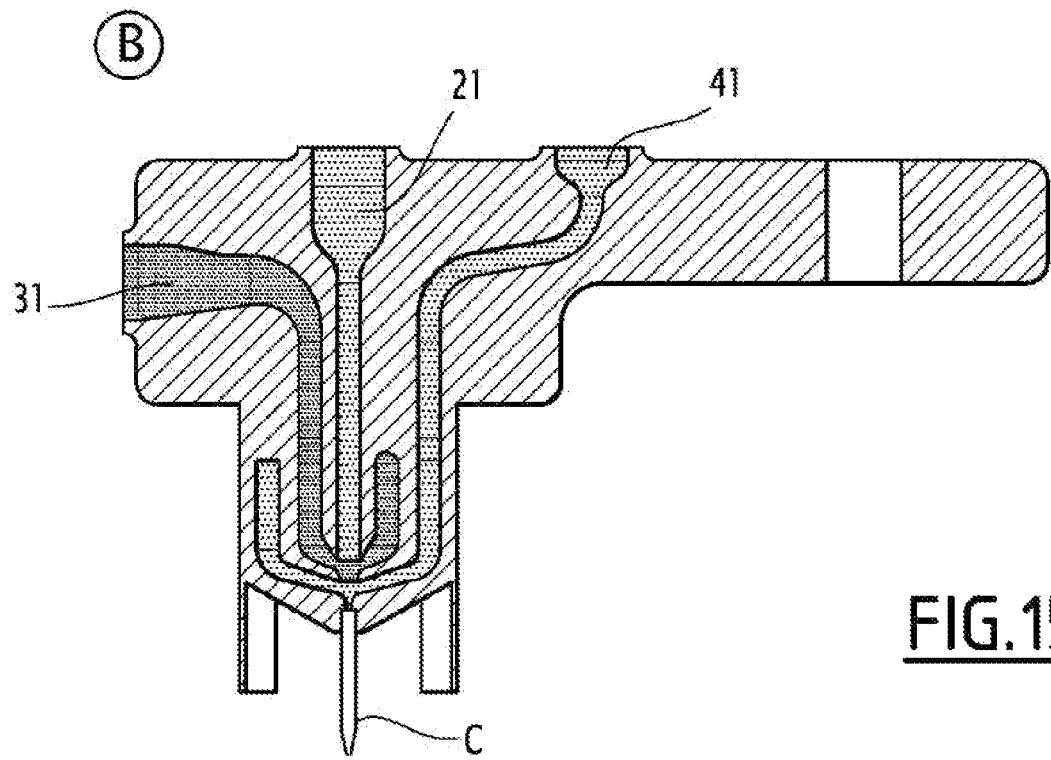

FIG. 15 (A) Schematic illustration of a middle transverse section of a two-way injector (B) Schematic illustration of a middle transverse section of a three-way injector.

EXAMPLES

Example 1

Experimental Conditions for Obtaining Gelled and Stiffened Capsules

Experimental Device

The method for preparing capsules is based on the concentric co-extrusion of compositions via a triple envelope device for forming multi-component drops (FIG. 15B).

A first composition (C1) circulating in a first compartment 21 of a triple envelope forms the first flow.

A second composition (C2) circulating in a second compartment 31 of the triple envelope forms the second flow.

A third composition (C3) circulating in a second compartment 41 of the triple envelope forms the third flow.

Formation of Gelled and Stiffened Capsules

At the outlet of the triple envelope, is then formed a multi-component drop, the first flow forming the liquid core, the second flow forming the liquid intermediate envelope and the third flow forming the liquid external envelope of the multi-component drop.

The size of the liquid core, the thickness of the intermediate envelope and of the external envelope of the formed capsules are controlled by using several independent syringe pumps, by adjusting the injection flow rates of the different compositions C1, C2 and C3.

The flow rate Q1 of the composition C1 is adjusted to 10 mL/h.

The flow rate Q2 of the composition C2 is adjusted to 1 mL/h.

The flow rate Q3 of the composition C3 is adjusted to 1 mL/h, and may be decreased down to 0.1 mL/h.

Each multi-component drop detaches from the triple envelope and falls in a volume of air, before being immersed in a gelling solution of 1M concentrated calcium lactate.

Once the external envelope is gelled, the gelled capsules formed are rinsed in a rinse solution based on water, and are then immersed in a stiffening bath.

Formation of Stiffened Capsules

The thereby formed gelled and stiffened capsules are then immersed in a depolymerisation solution of 10% concentrated citrate.

Once the external envelope is depolymerised and removed, the obtained stiffened capsules are rinsed in a rinse solution based on water and stored in a storage solution based on water.

Example 2: Capsules with a Double Envelope Based on Natural Latex/Alginate

The composition C1 is an aqueous solution of an amaranth colouring agent at 1 mM.

The composition C2 is an aqueous dispersion of natural latex (chemical name Cis 1,4-polyisoprene, family of dienes, example of a commercial natural latex: natural Rubber grade TSR, SRM, SIR, STR, SVR, ADS, RSS, Crepes, DPNR, from Astlett Rubber Inc.) diluted down to a 20% to 40% mass fraction of particulated polymers relatively to the total mass of the natural latex dispersion, also comprising 1% by mass of a surfactant of the ionic or non-ionic type depending on the grade.

In this example, the mass fraction of particles of polymers is set to 30% (the latex dispersion is titrated by gravimetry after washing by centrifugation) and the surfactant SDS (sodium dodecylsulfate) is used.

The composition C3 is an aqueous solution having a 2.0% mass percentage of sodium alginate and a 0.1% mass percentage of SDS.

The obtained capsules, with a standard diameter of few millimetres, are maintained in the gelling solution of calcium ions for one minute, and are then rinsed with distilled water. They are then stored in an isotonic solution relatively to the internal solution. Double coacervation by permeation of the calcium ions through the gelled alginate envelope is thus obtained. The capsules may then be incubated for 10 minutes in a 10% citrate solution in order to dissolve the outer membrane of alginate hydrogel. Capsules are thereby obtained, having an outer envelope of stiffened natural latex.

Example 3: Capsules with a Double Natural Latex/CB Alginate Envelope

Example 3 is obtained under the same conditions as Example 2, except that the composition C2 further comprises carbon black «CB: Carbon Black». To do this, a CB solution is prepared (from Carbon Black N234 from CABOT Corporation) in the presence of 2% SDS surfactant, the mass fraction of particles of polymers being still comprised between 20% and 40% based on the total mass of the natural latex dispersion. The CB fraction being comprised from 1% to 15%.

For this example, the mass fraction of particles of polymers is set to 30% and the mass fraction of CB to 5% based on the total mass of the composition C2.

After gelling the alginate envelope, the capsules are incubated in distilled water for about 20 minutes. The surfactant diffuses outwards from the capsules through the alginate envelope and causes coacervation of the mixed natural latex/CB mixture, giving rise to a stiffened envelope of reinforced rubber.

Example 4: Capsules with a Double Natural Latex/Colloidal Silica and Alginate Envelope Example 4 is produced under the same conditions as Example 2, except that the composition C2 further comprises colloidal silica with an average diameter of 100 nm (Aerosil from Degussa, Ludox from Sigma), according to mass fraction from 1% to 15% based on the total mass of the composition C2.

For this example, the mass fraction of particles of polymers is set to 30% and the mass fraction of colloidal silica to 5% based on the total mass of the composition C2.

Capsules are thereby obtained, including a stiffened envelope of reinforced rubber.

The prepared capsules according to the invention are easy to form, they have a resistant envelope, with a small thickness, which gives the possibility of ensuring efficient de-aggregation of the capsule when the liquid contained in the capsule has to be released.

Example 5: Capsules with a Simple Envelope Based on Alginate

I. Method

I.a. Making the Co-Extrusion Device

The central unit of the microfluidic devices consist in three glass capillary tubes co-aligned in the axial plane. The most external tapered capillary is obtained by stretching a rounded capillary in a transverse section (Vitrocom, internal diameter (i.d.) of 600 μm, an external diameter (e.d.) of 840 μm) with a micropipette structure (P2000, Sutter Instrument). The most internal capillary (i.d. of 100 μm, e.d. of 170 μm) and intermediate capillary (i.d. of 300 μm, e.d. of 400 μm) were maintained according to a cylindrical shape and were cut to the desired length. The ends of the capillaries were polished with micro-abrasive films (1 μm grain, 3M) in order to avoid any bevel shape generating perturbations in the flow and for obtaining the desired tip diameter (typically between 130 and 180 μm). A hydrophobic coating (1H,1H, 2H,2H-perfluorooctyltrimethoxysilane, ABCR) was applied on the walls of the capillaries according to standard procedures (Perret, E., et al. *Langmuir* 18, 846.-854 (2002)) in order to prevent any humidification of the external walls of the tip of the injector with the alginate solution. The assembling of the co-extrusion device was carried out under a binocular microscope. The most external capillary was first stuck to a glass slide which is used as a support for the device. Next, the two other cylindrical capillaries were inserted and sealed sequentially by using an epoxy resin (Loctite 3430, Radisopares-RS Components). The co-axial and longitudinal alignments were manually checked during the drying of the resin at room temperature. The inlet orifices of the chip were made by sticking syringe needle fittings to a foam end piece (NN-1950R, Terumo) at the top of the free ends of the capillaries.

I.B. Operation of the Co-Extrusion Device.

The three liquid phases (cell suspension CS, intermediate solution IS and alginate solution AL—see FIG. 6) were loaded into syringes (10MDR-LL-GT SGE, Analytical Science) provided with needles connected to Teflon tubes (Bohlender, inner diameter of 0.5 mm). The other ends of the tubes were inserted into suitable inlet orifices of the co-extrusion device, which is vertically clamped to an upright inside a laminary flow hood. The syringes were mounted on syringe pumps (PHD 4400, Harvard Apparatus) which control the injection of the liquids at the desired flow rates. In this work, the inventors mainly used two sets of flow rates: 1) for thin capsules: $q_{CS}$=50 ml h$^{-1}$, $q_{IS}$=50 ml h$^{-1}$, $q_{AL}$=40 ml h$^{-1}$, and 2) for thick capsules: $q_{CS}$=20 ml h$^{-1}$, $q_{IS}$=20 ml h$^{-1}$, $q_{AL}$=30 ml h$^{-1}$. After initiation of the flow rates, the micro-droplets of compounds are directed towards a gelling bath containing 100 mm calcium chloride (VWR) and trace amounts of the surfactant Tween 20 (Merck), and are placed at approximately 0.5 m below the outlet orifice of the device. Operation for a few seconds was sufficient for producing about $10^4$ capsules, which were immediately washed in an iso-osmotic sorbitol solution and transferred into a suitable culture medium. After use, the microfluidic device was cleaned with a disinfectant (Biocidal ZF, Biovalley), ethanol and de-ionised water. Before the next use, the chip was rinsed with a sorbitol solution.

I.C. Preparation of Aqueous Solutions and of Cell Suspensions.

The most external phase (AL solution) was prepared by dissolving 2.5% w/v sodium alginate (FMC, Protanal LF200S) in water, and by adding 0.5 mM of sodium dodecylsulfate surfactant (SDS) (VWR). The solution was filtered at 1 μm (Pall Life Science) and was stored at 4 C. The intermediate phase (IS) is generally a 300 mM sorbitol solution (Merck). The most internal phase (CS) was obtained by detaching the cells from the walls of the culture flask with a 0.5% EDTA-trypsin (Invitrogen). After washing in the suitable culture medium and delicate centrifugation (300×g, 5 minutes, 20° C.), they are re-suspended in a 300 mM sorbitol solution at an approximate concentration of 3×10$^6$ cells per ml.

I.D. Cell Lines, Monolayer and Cultures of Encapsulated Cells.

The inventors used carcinoma cells from the murine colon of the wild type CT26 (purchased from the American Tissue Culture Collection, ATCC CRL-2638) and the CT26 cells stably transfected with LifeAct-mCherry. Tests were also conducted with HeLa cells and murine sarcoma cells (S180, kind donation from Chu Yeh-Shiu, IMCB, Singapore).

All the cells were maintained in Dulbecco's Modified Eagle Medium (DMEM, Invitrogen) supplemented with foetal calf serum at 10% (FBS, Invitrogen) and antibiotics (100 μg ml$^{-1}$ of Streptomycin and 100 units ml$^{-1}$ of Penicillin (Gibco BRL) in a humidified atmosphere containing 5% CO$_2$ at 37° C. by replacing the medium every 2 days. The cells were cultivated in the form of sub-confluents monolayers in order to prepare the cell suspensions used for encapsulation in hollow alginate spheres.

Once the cell capsules were formed by following the procedure described above, they were placed inside an incubator (37° C., 5% CO$_2$ at about 100% of relative humidity). Among the thousands of collected cell capsules, the majority was maintained in a Petri dish containing a culture medium and were cultivated under the same conditions as the cell monolayers. In each encapsulation cycle, several tens of capsules were selected for high resolution imaging. Depending on the requirements for configuring the microscope and on the desired duration of the imaging session (from a few hours to a few weeks), these selected cell capsules were transferred into dedicated culture chambers or devices (see the description below).

As a comparison with our method, CT26 spheroids were also cultivated according to the standard technique on a bed of agarose (Hirschhaeuser, F. et al. J. Biotechnol. 148, 3.-15 (2010)).

I.E. Colouration of the Fixed Spheroids.

The spheroids were fixed in 4% PFA in PBS for 1 hour at room temperature. For the colouration of the cortical actin, they were incubated with 0.5 µg ml$^{-1}$ of phalloidin conjugate with Alexa488 (Molecular Probes) in a PBS solution with Triton-X100 at 1% v/v (Sigma) at 4° C. for 2 hours overnight. Immunological marking of fibronectin was carried out according to a standard procedure. Briefly, the spheroids were permeablised by using Triton-X100 at 2% v/v in PBS. The primary antibodies (anti-fibronectin antibodies produced in a rabbit, Sigma) and secondary antibodies (anti-rabbit goat IgG (H+L) conjugate with Alexa Fluor568, Invitrogen) were diluted to 1/250 and are then incubated for 12 hours.

I.F. Evaluation of Cell Viability and Cell Count.

In order to evaluate the effectiveness of the encapsulation and the concentration of cell seeding, phase contrast images of the capsules were immediately taken after encapsulation and a number of cells per capsule was estimated by using standard ImageJ plugins (Schneider, C. A., et al. *Nat. Methods* 9, 671.-675 (2012)).

The cell viability was characterised at different stages of the cell culture encapsulated with colouring agents for live/dead cells, calcein AM/ethidium homodimer-1 (EthD-1) (Invitrogen). In order to evaluate the potential obnoxiousness of the encapsulation method on suspended cells, the inventors incubated the cell capsules immediately after formation with EthD-1 at 4 µM and calcein AM at 2.5 µM for 30 minutes to 1 hour. The number of viable cells was determined by counting the red cells (dead) and the green cells (living) by using an inverted epifluorescence microscope (Axiovert-200M, Carl Zeiss) equipped with an Hg lamp and an EM CCD camera (C 9100-02, Hamamatsu Photonics). As a comparison, the same measurements were conducted on the cell suspension before encapsulation. When the spheroids were formed and were subject to expansion within the capsules, the same procedure was adapted by increasing the concentrations of the colouring agents by ten times and the incubation duration from 2 to 4 hours. The equatorial planes of the spheroids were then viewed as confocal microscopy images. While the red cells (dead) may be detected in the core of the spheroids, the living cells were practically not coloured beyond a peripheral edge of a few layers. This layer internal marking is due to the fact that the ubiquitous intracellular esterase activity of the peripheral cells is sufficient for esterifying all the calcein AM molecules permeable to the cells before they may penetrate more deeply into the spheroid.

I.G. Imaging the Growth of Spheroids in the Long Run and of the Deformation of the Capsules.

The growth of MCSes inside the capsules and the deformation of the shell were monitored by phase contrast microscopy. For all the encapsulation sessions, 24 capsules were selected from the entire batch of cell capsules and were individually transferred into each well of a multi-well culture plate (Falcon). Each capsule was viewed in the form of images every 3 hours with an inverted microscope Nikon EZ (dry objectives 10×/0.25 NA or 20×/0.4 NA) equipped with a colour CCD camera (Nikon Digital sight DS Fi1) driven by the software package NIS Element. Capturing the images was carried out at room temperature and lasted for approximately 5 minutes. Between each acquisition, the 24-well plate containing the capsules was maintained in the incubator. Half of the culture medium was renewed every two days. For acquiring real time sequences at a higher time resolution (1 sequence every 5 minutes) over extended time periods (about 15 days), the inventors also used a reverted microscope (Nikon Eclipse Ti, dry objective 10×/NA0.3) equipped with a motor driven stage (Märzhäuser) and a system for controlling the climate (The Brick, Life Imaging Systems). The microscope and the camera (CoolSNAP HQ$^2$, Photometrics) were driven by the Metamorph software package (Molecular Devices). In order to prevent any displacement or drift of the capsules in the well outside the field of view, the inventors designed an observation chamber custom-made. Phytagel (Sigma) wells of the following type were prepared by using conical moulds in PDMS (polydimethylsiloxane elastomer, Sylgard-184, Dow Corning) adapted to the wells of a 24-well plate with glass bottoms (Radnor, Pa.). This configuration facilitates the loading of the individual capsules, which are directed towards the centre of the well. The orifices (a diameter of 500 µm) in the phytagel replicas, which are mainly used as a micro-conduit, also prove to be effective for limiting the movements of the encapsulating spheroids, and this without inducing stressors which may alter the growth of the MCS.

I.H. Imaging the 3D Cell Organisation of the Encapsulated Spheroids.

In order to view the peripheral cell layers and the core of the spheroids in expansion at a subcellular resolution, the inventors used confocal microscopy with single photon or multiphoton fluorescence.

Confocal imaging of living cells was achieved by using an inverted microscope (LSM710, Carl Zeiss) equipped with a climate regulation chamber (Pecon) controlling the $CO_2$ percentage, the temperature and the humidity. The samples were prepared by immersing the capsules in a solution of agarose with a low melting point at 0.3% (Invitrogen) (a culture medium without any serum, 37° C.) in a Petri dish with a glass bottom tailor made (diameter of the wells of about 2 mm). After gelling granules of agarose (10 minutes, room temperature), the Petri dish was filled with the culture medium. This assembly gave the possibility of immobilising the capsules, a step required for acquiring images with the «z-stack acquisition» method (automated acquisition of several images XY along the axis Z). The percentage of agarose was selected in order to generate a minimum stress on the MCSes in expansion. A comparison of the growth kinetics between the MCSes moving freely and the MCSes incorporated into the agarose did not reveal any significant difference. In order to monitor the cell dynamics within the spheroids, we used the cell line CT26 stably transfected with LifeAct-mCherry or CT26 cells of the wild type incubated in FM4-64 (Invitrogen, 2 µg ml$^{-1}$). The fluorescence was acquired by using a laser pumped by solid state diode at 561 nm (15 mW) and an objective with immersion in oil 25×/0.80 NA. The images of the surface of the fixed spheroids coloured with phalloidin-Alexa488 were viewed with an argon laser at 488 nm (25 mW) and an objective with immersion in oil 63×11.4. The individual images and the stacks of images were processed by using the software package Zen 2011 (Carl Zeiss) and ImageJ or Fiji (Schindelin, J. et al. *Nature Methods* 9, 676.-682 (2012)). Videos online were edited by using After Effects and were then compressed by using Media Encoder (Adobe).

A multi-photon microscope was used for accessing the core of the encapsulated spheroids. Two types of microscopes were used: 1) a vertical two-photon laser scanning microscope (Lavision) equipped with an objective with immersion in water 20×/0.95 NA (Olympus); 2) an inverted microscope LSM710 NLO (Carl Zeiss) equipped with objectives with immersion in oil 25×/0.80 NA or with immersion in water 40×/1 NA (Carl Zeiss). The configurations were coupled with femtosecond lasers (690-1020 nm, from Coherent or Spectra Physics). The images of the inside of the fixed spheroids coloured by phalloidin-Alexa488 were acquired at a laser wavelength of 920 nm. Sulforhodamine B (SRB, Sigma) was added to the medium at a concentration of 40 µg ml$^{-1}$. The best conditions for live imaging of the spheroids in a culture medium supplemented with SRB was obtained for an excitation at 800 nm (Marmottant, P. et al. *Proc. Natl. Acad. Sci. U.S.A.* 106, 17271.-17275 (2009)). The capsules were mounted as described for the single photon confocal live imaging.

I.I. Morphometric Measurements of the Capsules.

The characterisation of the sizes and of the shapes of the capsules was determined on capsules containing the cells and on empty capsules. The measurements on the empty capsules, which were obtained by replacing the CS phase with an iso-osmotic sorbitol solution, were conducted immediately after encapsulation and after a week of dwelling in the culture medium at 37° C. (in order to take into account potential morphological modifications induced by ageing). No significant difference was observed between these diverse conditions. The images of large fields for viewing densely grouped capsules were acquired with phase contrast microscopy and were analysed by using the ImageJ. The average radius of the capsule is defined as: $R=\sqrt{S/\pi}$, wherein S is the equatorial transverse surface of the capsule. The circularity of the capsule was measured as a ratio of the minor axis over the major axis of the ellipse adjusted to the external edge of the projected equatorial section.

When the spheroids are at confluence, the external and internal walls of the capsule may be easily detected because of the high optical contrast. On the other hand, for empty or partly filled capsules, the internal wall of the capsule is slightly visible by phase contrast microscopy. The measurements of the thickness of the capsule were therefore conducted by doping the alginate solution with 250 µg/ml of FITC-dextran with a high molecular weight (2 MDa, Sigma). The images of the capsules were acquired by confocal microscopy and were analysed with ImageJ. The influence of low flow rates on the aspect ratio h/R$_{out}$ was evaluated by comparing the experimental data with the theoretical value calculated from the conservation of the volume:

$$\frac{h}{R_{out}} = 1 - \left(\frac{q_{in}/q_{out}}{1+q_{in}/q_{out}}\right)^{1/3}$$

I.J. Measurements of the Elasticity of the Alginate Gels.

Three different methods were used for measuring Young's modulus of the alginate gels.

The inventors first conducted measurements of microindentation by AFM on empty capsules.

Alginate capsules positioned at the bottom of a Petri dish filled with a culture medium were placed on the sample stage of an AFM system Catalyst (Bruker) mounted on an inverted optical microscope (1×71, Olympus) in a force mode (FIG. 9A). The inventors used TR400 cantilevers attached to spherical SiO$_2$ beads (diameter of 5 µm) and having a rated stiffness constant k$_{cantilever}$=0.06 N/m (Novascan). The sensitivity of the photodiodes was calibrated before and after measurements on a freshly cleaved mica surface in PBS. The stiffness constant was determined by using the method of thermal fluctuations applied in the software package Bruket Nanoscope 7.2. The force-distance curves (F-z) were recorded for displacements of a peak-to-peak amplitude of about 2 µm at 0.25-1 Hz. The relative deflection threshold was controlled for attaining a capsule deformation comprised between 200 nm and 500 nm. The data were analysed within the scope of an indentation of the punctual load in hollow spheres. The functional force (F)–deformation (δ) relationship (Fery, A. & Weinkamer, R. Polymer 48, 7221.-7235 (2007)) is the following:

$$F = \frac{4}{3\sqrt{1-v^2}} E \frac{h^2}{R} \delta.$$

The deformation was calculated in terms of a contact point (z$_c$) and of the shift of the deflection (d$_0$) as d=z−z$_c$−(d−d$_0$). Experimentally, Young's modulus of the alginate gel was derived from adjustment of the force-deformation traces (FIG. 9A) by taking the values measured for the geometrical properties (R and h) of the capsule and v=0.5 for the Poisson ratio. The inventors observed that E=55±44 kPa (±SD, N=7).

The second method consists of conducting measurements of the traction on macroscopic alginate gel cylinders of the spaghetti type. These threads (length L$_0$ of about 0.2 m, diameter D$_0$ of about 1 mm) were formed with a simple 1 way extrusion device provided with an end piece with a size of about 1 mm, by immersing the tip in the calcium bath in order to suppress the instability of the capillary. A controlled stress σ was applied with a set of calibrated weights m suspended from the alginate cylinders. The elongation ΔL/L$_0$ of the alginate sample was measured with a ruler. By supposing that v=0.5, the Young modulus was derived from $$\sigma = \frac{4 \, mg}{\pi D_0^2 (1 - \Delta L/L_0)} = E \cdot \frac{\Delta L}{L_0}.$$

The inventors observed that E=71±12 kPa (±SD, N=9).

A third determination of E is based on an osmotic inflation test. For this purpose, the inventors replaced the cell suspension with a sorbitol solution with 5% w/v dextran, P$_m$=2 MDa and 500 kDa (Sigma Biochemika). The calcium bath solution and the storage culture medium were also supplemented with 5% w/v dextran. Iso-osmotic equilibrium of all the solutions was controlled. In order to obtain a detectable inflation, capsules with very thin walls were prepared (q$_{in}$/q$_{out}$=10, which corresponds to a shell thickness h of about 5-7 µm). Stepwise dilution of dextran caused osmotic inflation of the capsules. The differences in concentration in the dextran were converted into osmotic pressures π$_0$ and the expansion of the capsules ΔR/R$_0$ was directly measured. To the first order, in the limit of a slight deformation, the Young's modulus of the alginate was derived by balancing the elastic energy of the spherical shell and the effect obtained by the osmotic pressure difference:

$$E \approx \frac{1}{4h_0/R_0} \cdot \left(\frac{\Delta R/R_0}{\pi_0}\right)^{-1}$$

I.K. Determination of Young's Modulus of an Alginate Gel from the Osmotic Inflation of a Capsule Considering a spherical capsule consisting of an alginate shell containing a high molecular weight dextran solution ($P_m$=500 kDa or 2 MDa) immersed in a less concentrated dextran solution, given that the shell is permeable to water (estimated porosity of about 6 nm) but not to dextran (Stokes radii between about 15 nm and 27 nm), the water molecules diffused into the capsule, which inflates until the elastic force of the stretched capsule balances the osmotic pressure.

At the beginning of the test, the dextran concentrations inside and outside the capsule are equivalent. The initial radius of the capsule is $R_0$, and the dextran concentration in the external bath is then reduced by dilution, so that the concentration difference is $c_0$. During the inflation, the radius of the capsule increases by $\Delta R = R - R_0$ and the concentration difference is reduced from $c_0$ to c:

$$c = c_0 \cdot \left(\frac{R_0}{R}\right)^3. \quad (1)$$

The stretching elastic energy is given by (Landau, L. D., et al. Theory of Elasticity, Third Edition: Volume 7. (Butterworth-Heinemann: 1986)):

$$G_{el} = 4\pi \frac{E}{1-v} h(R-R_0)^2, \quad (2)$$

wherein h is the thickness of the shell and v is the Poisson ratio. For an incompressible material, v=½ and the shell becomes thinner when the capsule inflates, according to:

$$h = h_o \cdot \left(\frac{R_o}{R}\right)^2, \quad (3)$$

wherein $h_0$ is the thickness of the unstretched capsule.

Given that solutes are very bulky, the osmotic pressure Π significantly deviates relatively to the rated value ($\Pi=nk_BT$, wherein n is the number of active species from an osmotic point of view and $k_BT$ is the thermal energy) and proves to be independent of their rated osmolality beyond a given threshold ($P_m$=200 kDa for dextran) (Reid, C. & Rand, R. P *Biophys J* 73, 1692-1694 (1997)). Different empirical expressions are reported for adjusting the data of the osmotic pressure (Veretout, F *Journal of molecular biology* 205, 713-728; Bonnet-Gonnet, C. et al. *Langmuir* 10, 4012-4021 (1994)). For simplicity purposes, we consider the polynomial expression well established for π as a function of c (in weight/volume percentage):

$$\Pi=\alpha c+\beta c^2+\gamma c^3 \quad (4),$$

wherein α=286, β=57 et γ=5. The effect generated by the osmotic pressure for inflating the capsule from $R_0$ to R is given by:

$$W=\int_{R_o}^{R}\Pi \cdot 4\pi R^2 dR \quad (5).$$

By taking into account the dilution effect (Eq. 1), we obtain:

$$W = 4\pi R_0^3 \left(\alpha c_0 \ln\left(\frac{R}{R_0}\right) + \frac{1}{3}\beta c_0^2\left(1 - \left(\frac{R_0}{R}\right)^3\right) + \frac{1}{6}\gamma c_0^3\left(1 - \left(\frac{R_0}{R}\right)^6\right)\right). \quad (6)$$

The radius of the capsule at equilibrium is indicated by the minimum of the total energy $G_{el}$+W. Further by assuming small deformations, $\Delta R/R_0 \ll 1$, we reach:

$$\frac{\Delta R}{R_0} = \frac{\Pi_0}{\Pi_c + 4E(h_0/R_0)}, \quad (7)$$

wherein $\Pi_0$ is the osmotic pressure at $c_0$, and $\Pi_c = \Pi_0 + 3\beta c_0^2 + 6\gamma c_0^3$.

This reveals that the osmotic pressure $\Pi_0$ varies from 0 to 4 kPa within the explored range of differences in concentrations. The approximation indicated above lies on the assumption that the correction introduced by $\Pi_c$ remains negligible relatively to the effective Young modulus $E \times 4h_0/R_0$. By assuming E=68 kPa and $h_0/R_0$ is about 0.05, this is only valid for $c_0$<2%. Under our experimental conditions ($c_0$ varying from 0 to practically 5%), a more accurate determination of E requires the use of Eq. 7.

I.L. Analysis of the Growth of the Spheroids and of the Deformation of the Capsules.

The phase contrast real time images were analysed by using an algorithm for detecting ages based on the gradient and tailor made, applied in Matlab (MathWorks). By beginning from the centre of the capsule, the intensity profiles were acquired in a radial position and were inspected in order to identify the peaks in the first derivative in order to extract the contour of the MCS and of the capsule containing it in each recorded structure. $R_{out}$ was derived from the projected transverse surface. A similar approach was followed for monitoring $R_{MCS}$ inside the capsule. The background noise detected before confluence was mainly due to rotary movements of the non-perfectly spherical cell aggregate. The confluence time (t=0) was determined as the time for which the growth of the MCSes exhibits an inflexion point. The inventors checked that this time coincided, in less than 5 minutes, with the visual determination of confluence (on high time resolution videos). The pre- and post-confluence stages were also quantified by a roughness parameter, $\rho=P/2\sqrt{\pi A}$, P and A respectively being the perimeter and the surface area of an equatorial transverse section. Whereas the time-dependent change in row has a background noise during the first stages of the growth of the MCS, it decreases when the spheroid approaches the wall of the capsule, before it is saturated to a minimum value close to the theoretical value of 1 for perfectly spherical objects.

I.M. Phenomenological Approach for Non-Linear Elasticity of Alginate Capsules at Significant Deformations In order to confirm the measurement of Young's modulus derived from the osmotic inflation test, the inventors developed a second mechanical test, consisting of directly evaluating the stress (σ)-deformation (ε) relationship of the alginate gel threads. These threads (diameter of 1 mm) were stretched with calibrated weight to which were welded tiny alginate droplets at one end. Under low deformation conditions, (typically for the relative elongation $\epsilon=\Delta L/L_0$<10%), the stress-deformation response is linear and the derived Young's modulus is quite compliant with the one measured earlier (E=71±12 kPa). In the case of a highly significant deformation greater than (>80%), water formed from the sample and significant plasticity was obvious. For the intermediate deformation, the material has a non-linear stress-deformation response (FIG. 9B). Such a hardening behaviour at a stress is quite common for biopolymer gels and has already been reported for alginate gels (Zhang, J., et al. 2007 Journal of Food Engineering 80, 157-165). Given that the thin capsules (h/R of about 0.1) which were considerably used in this work exhibit a maximum radial deformation $\Delta R/R_0$ of about 30% before bursting, an accurate determination of the pressure exerted by the confined spheroid in expansion require that this effect be taken into account. A standard phenomenological approach for non-linear elasticity consists of considering a corrective term in $\varepsilon^2$ for the stress ($\sigma = E_\varepsilon + A_\varepsilon^2$). Conversely, by adjusting the $\sigma$–$\varepsilon$ with a polynomial expression of the second order, the inventors defined an effective elastic modulus depending on the deformation $E_{\mathit{eff}}(\varepsilon) = E(1 + a\varepsilon)$ and we observed $\alpha = 1.5$. We used this expression for E in order to derive the pressure from deformation data on thin capsules.

I.N. Expansion of a Spherical Container with Thick Walls Subject to Internal Pressure The inventors have assumed that the alginate gel is isotropic and that the deformations are small (i.e. <10%). On the other hand, if the condition h/R«1 is not satisfied, the assumption of a constant tangential stress through the thickness of the container is not valid. In the general case of a Poisson ratio $v \neq \frac{1}{2}$, the inventors have to resort to expressions for the radial and circumferential stress (Fung, Y. C. Foundations of Solid Mechanics; Prentice Hall: 1965):

$$\sigma_r = \frac{PR_{in}^3}{R_{out}^3 - R_{in}^3}\left(1 - \frac{R_{out}^3}{R^3}\right) \qquad (1)$$

$$\sigma_\varphi = \frac{PR_{in}^3}{R_{out}^3 - R_{in}^3}\left(2 + \frac{R_{out}^3}{R^3}\right), \qquad (2)$$

wherein $R_{in} \leq R \leq R_{out}$.

The radial displacement u(R) is obtained from Hooke's law:

$$u(R) = \frac{(1-v)\sigma_r - v\sigma_\varphi}{E}R. \qquad (3)$$

By collecting these results, the inventors reached:

$$u(R) = \frac{P}{E}\frac{PR_{in}^3}{R_{out}^3 - R_{in}^3}\left[(1-2v)R + \frac{(1+v)}{2}\frac{R_{out}^3}{R^2}\right]. \qquad (4)$$

If the material is incompressible, this equation may be simplified and applied for two particular cases of interest, notably $R = R_{in}$ et $R = R_{out}$:

$$u(R_{in}) = \frac{3}{4}\frac{P}{E}\frac{R_{in}}{1 - (R_{in}/R_{out})^3}, \qquad (5)$$

$$u(R_{out}) = \frac{3}{4}\frac{P}{E}\frac{R_{in}}{(R_{out}/R_{in})^3 - 1}. \qquad (6)$$

Finally, from the conservation of the volume of the shell, we have:

$$R_{out}^3(t) - R_{in}^3(t) = R_{out}^3(0) - R_{in}^3(0) = \Delta(R_0^3) \qquad (7).$$

By using this equation, the two time variables $R_{in}(t)$ and $R_{out}(t)$ are separated and the pressure P(t) is written in function of either of $R_{in}(t)$ or $R_{out}(t)$. Experimentally, only the initial external and internal radii therefore have to be measured and the time dependent change of the internal or external radius of the capsule has to be followed.

$$P(t) = \frac{4}{3}E\left[1 - \frac{1}{1 + \Delta(R_0^3)/R_{in}^3(t)}\right]\frac{u(R_{in}(t))}{R_{in}(t)}, \qquad (8)$$

$$P(t) = \frac{4}{3}E\left[\frac{1}{1 - \Delta(R_0^3)/R_{out}^3(t)} - 1\right]\frac{u(R_{out}(t))}{R_{out}(t)}. \qquad (9)$$

Let us note, that by returning to the general case described by Eq. (4) and by constructing the ratio of the displacements at the internal and external surfaces, it is found (Dym, C. L. & Williams, H. E. (2007) International Journal of Mechanical Engineering Education 35, 108-113):

$$\frac{u(R_{out})}{u(R_{in})} = \frac{3(1-v)\rho}{2(1-2v) + (1+v)\rho^3}, \qquad (10)$$

wherein $\rho = R_{out}/R_{in} > 1$.

First of all, given that this ratio is always less than one, the displacement at the external radius is smaller than that at the internal radius, which is intuitive and experimentally observed. Next, $u(R_{out})/u(R_{in})$ provides a direct estimation of the Poisson ratio, which prove to be $v = \frac{1}{2}$.

II Results

II.A Formation of Alginate Microcapsules Assisted with a Microfluidic Device

The procedure for preparing the cell microcapsules is inspired from the method developed for making liquid pearls of the order of one millimetre and is further adapted for reducing the diameter of the capsules and reaching the requirements of a cell culture. The fundamental operation principle consists of generating a hydrogel shells containing a suspension of cells by co-extrusion (FIG. 6A). More specifically, the microfluid device is assembled by co-centring of three glass capillaries (FIG. 6B). The cell suspension circulates in the most internal capillary while an alginate solution is injected in the most external tapered capillary. Gelling of the alginate shell is achieved out of the chip in a calcium bath. An intermediate capillary filled with a solution without any calcium is used as a barrier to the diffusion of the released from intracellular stocks and thus avoids blocking of the chip. The inventors also modified the mode of formation of the droplets. At flow rates q, the liquid froze drop-wise from the capillary and produces capsules with a size of 2-3 mm (FIG. 6C), as a consequence of the interaction between gravity and surface tension. In contrast, at a higher flow rate q, the liquid emerges as a jet, which is dispersed into droplets downstream because of the instability of the capillary. It is then expected that the size of the droplets be closely associated with the diameter D of the orifice. A lower limit for the flow rate of the liquid is defined by the condition for occurrence of the dropwise-jet transition, i.e. for a critical Weber number $pV^2D/\sigma \approx 4$ with a liquid in the non-viscous limit and with low gravity. By neglecting the structure of the flow in three phases and assuming a simple liquid with $\rho = 10^3$ kg m$^{-3}$, $\sigma = 50$ mN m$^{-2}$, one obtains $V_{min} \sim 1$ m s$^{-1}$, and $q_{min} = \pi(D/2)^2 V_{min}$ of the order of ~40 ml h$^{-1}$ for D=130 µm. An upper limit for q is controlled by the height of the fall: the distance d between the end piece and the gelling bath surface should be greater than the intact length of the jet, which may attain 10 to 100×D (FIG. 6c), depending on q and external perturbations. On the other hand, the inventors have observed that increasing d promoted the coalescence of two consecutive drops before gelling, which finally generated larger capsules of an ellipsoidal shape. Up till now, the inventors had neglected the fact that the core of the droplet, the shell and the gelling bath were aqueous phases therefore are priori miscible. In order to avoid any mixing, the inventors added trace amounts of surfactant to the alginate solution and to the surface of the gelling bath, which reduces the surface tension and imparts transient stiffness to the drop of compound during the impact.

II. B Characterisation of the Microcapsules

Figure 1:
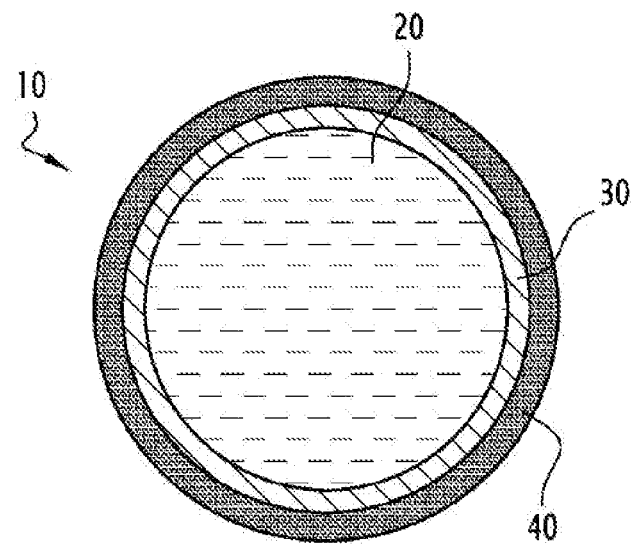
FIG. 1 is a large scale view in a section along a middle vertical plane of a gelled and stiffened capsule according to the invention.
Figure 2:
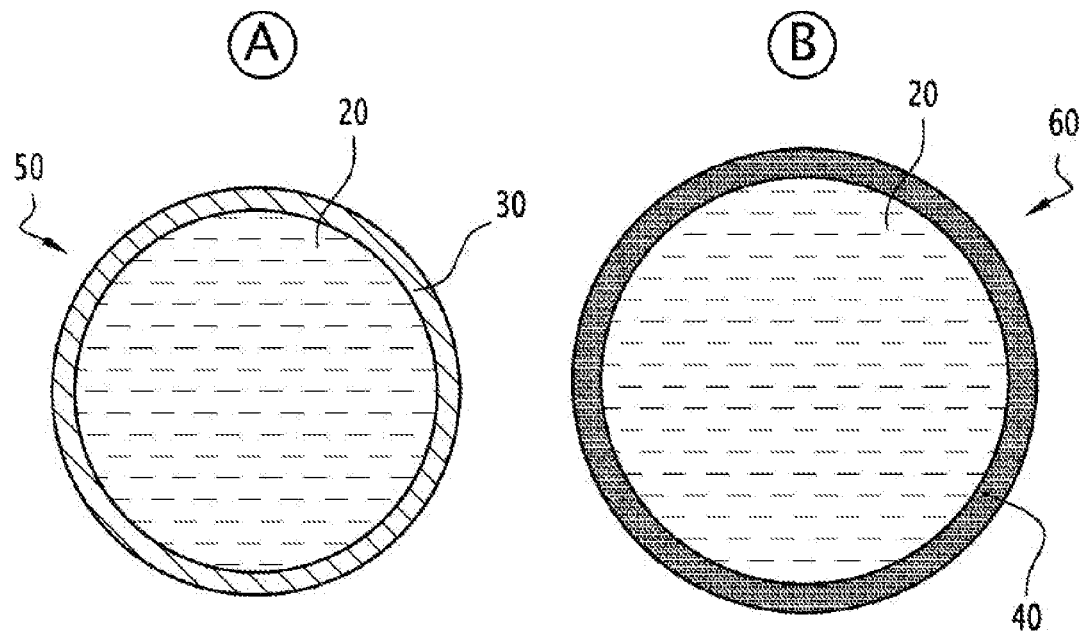
FIG. 2 is a large scale view, in a section along a middle vertical plane of a stiffened (A) or gelled (B) capsule according to the invention.
Figure 3:
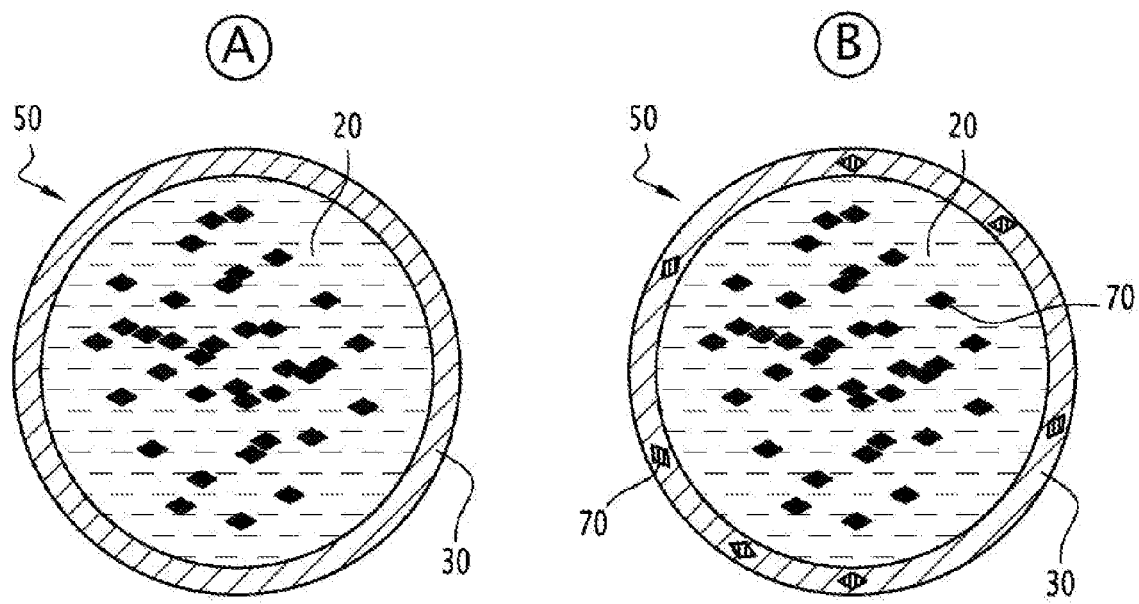
FIG. 3 is a large scale view, in a section along a middle vertical plane of a stiffened capsule for which the liquid core contains eukaryotic cells (A) and for which the liquid core and the stiffened envelope (B) contain eukaryotic cells.
Figure 4:
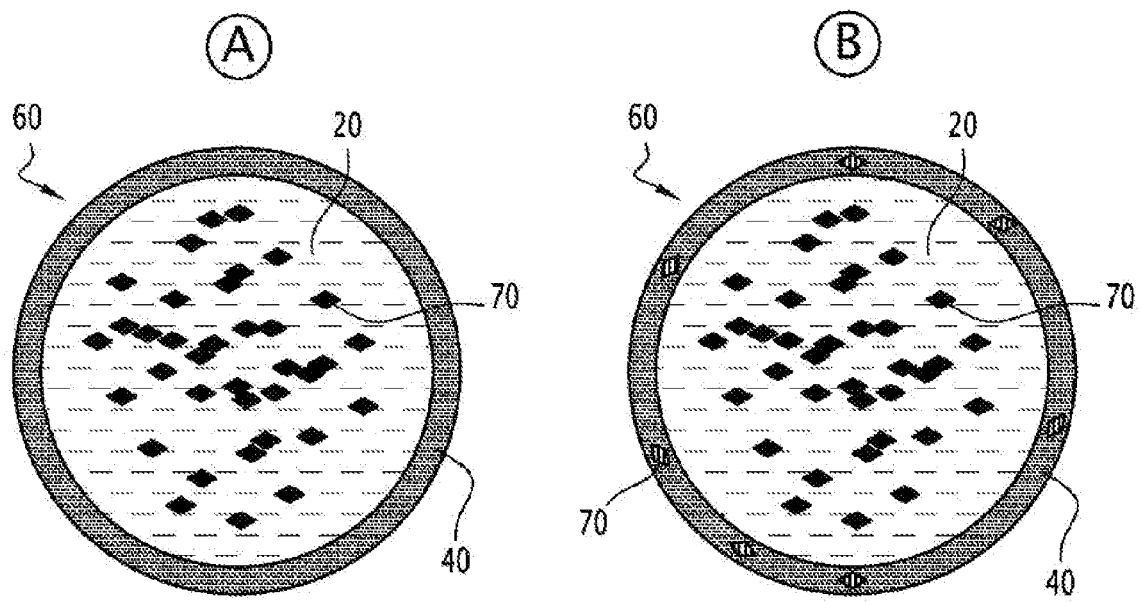
FIG. 4 is a large scale view, in a section along a middle vertical plane of a gelled capsule for which the liquid core contains eukaryotic cells (A) or for which the liquid core and the gelled envelope (B) contain eukaryotic cells.

In a typical experiment, approximately half of the capsules are spherical (as determined by the circularity parameter >0.8) and monodispersed (FIG. 7A). The production rate of the capsules (>$10^4$ $s^{-1}$) is sufficiently high for allowing rapid manual selection of 10-100 capsules of spherical shape. Although it is possible to increase the fraction of the spheres by forcing instability of the capillary by controlled flow perturbations, slight anisotropy will always be present because of the presence of a small tail which is inherent to the impact in the gelling bath. However, this anisotropy has a negligible effect on the mechanical measurements reported below. It is expected that the average size of the droplets of compound be determined by the fastest growth mode $2\pi/\lambda$ of the Rayleigh instability. Given that $\lambda$ is proportional to the diameter of the liquid jet $d_{jet}$ for a given viscosity contrast, the conservation of the volume between a cylinder of length $\lambda$ and of section $\pi d_{jet}^2/4$ and a drop of a radius R causes R=$d_{jet}$. For most operational conditions, the diameter of the end piece was D=130 µm≈$d_{jet}$, by producing an average drop size R=148±21 µm, which is compliant with the theoretical prediction of the first order. The thickness of the shell may be measured in confocal imaging by colouration with fluorescent dextran of high molecular weight of an alginate capsule. Such an observation gives the possibility of observing a clear separation of the shell from the cell suspension and from the intermediate solution of the capsule, a reduced mixture of the constituents of the capsule. Thus, the thickness of the shell h may be measured with accuracy. However, in a more interesting way, h may be adjusted by varying the ratio between the internal flow rate $q_{in}$ (sum of the flow rates of the cell suspension and of the intermediate solution) and the external flow rate $q_{out}$ of the alginate solution. Modifications of the ratio $q_{in}/q_{out}$ mainly have an effect on the aspect ratio h/$R_{out}$ (FIG. 2d), $R_{out}$ being the external radius of the capsule. The production of capsules with very thin walls is limited by the fragility of the shell. However, an increase in the alginate flow rate aiming at producing very thick shells will tend to generate heterogeneous and deformed capsules. In practice, for capsules with a radius of about 150 µm, h may vary, completely reliably, between 5 and 35 µm (FIG. 7B).

The inventors also studied the mechanical properties of alginate capsules. Quite surprisingly, the rheology of alginate gels is still an object of debate. Except for the discrepancies observed between studies which use distinct techniques, the Young modulus E of alginate gels, which characterise the stiffness of the raw material, depends on many parameters (alginate concentration, chemical composition, nature and concentration of cross-linking cations). In order to avoid any variability depending on the procedure, the inventors directly evaluated the elasticity of the raw gel of the capsules by using an osmotic inflation test. According to the deformation of capsules pre-loaded with high molecular weight dextran and immersed in a solution gradually depleted of dextran, the inventors derived E=68±21 kPa (FIGS. 8A and 8B, example 5 Methods). This value was further confirmed by a micro-indentation test with AFM (FIG. 9A) and a macroscopic elongation of raw alginate cylinders (FIG. 9B). Even if the alginate gels have a particular structure illustrated by the egg box model, an approximate relationship valid for cross-linked polymer gels reticules[27], E/3=kT/$\xi^3$, gives the possibility of estimating the average size of the meshes of the gel $\xi$=6 nm, which is sufficiently significant so that globular proteins with a $P_m$ of about 150 kDa may diffuse through the latter. No hysteresis was observed during osmotic inflation-shrinking cycles and no time-dependent change in the deformation was detected when the osmotic pressure difference was maintained for longer time periods (data not shown), which suggests that the hydrogel behaves like a purely elastic material.

II.C Quantitative Analysis of the Growth of a Spheroid Confined in an Elastic Environment In order to obtain a quantitative description of the impact of the elastic confinement on the growth of MCSes, the inventors adjusted the stiffness, $k_{caps}$, of the capsules by varying the thickness of the shell ($k_{caps}\propto E\times h$) and monitored the time-dependent change of the average radius of the spheroids, $R_{MCS}$(t), by using microscopy/real time video. Three distinct phases were observed. During phase 1, before confluence (t<0), the $R_{MCS}$ rapidly increases at similar rates in the thick and thin capsules (FIG. 11A). The spheroid freely grows inside the capsule at a constant growth rate, $\dot{V}/V$=3$\dot{R}_{MCS}/R_{MCS}$≈1.25 (jour)$^{-1}$, which is similar to the doubling rate of 2D cell monolayers (FIGS. 11B and 13A). Phase 2 typically begins when the $R_{MCS}$ approaches the internal radius of the shell $R_{in}$ within a single cell size (about 10 µm). At t=0 (confluence), the apparent growth rate $\dot{V}/V$ decreases by about three times. Phase 2 corresponds to the smoothing transition, and approximately last from t=−1 day to t=+1 day (FIG. 11B). During phase 3 (t>0), the $R_{MCS}$ is practically stabilised for thick capsules and continues to slowly increase for thin capsules (FIG. 11A). An in-depth inspection reveals that $\dot{V}/V$ drops by more than one order of magnitude as compared with the free growth of the MCS, but never becomes strictly equal or zero (FIG. 11B). The average of approximately 20 capsules indicates that $\dot{V}/V$ in phase 3 is of about 0.07 (day)$^{-1}$ for thin capsules and 0.04 (day)$^{-1}$ for thick capsules (FIG. 13A).

From a qualitative point of view, even if a slower growth is expected in the case of confinement in stiffer capsules, a quantitative explanation requires that the pressure exerted by the expanding MCS be derived. As a first approximation, the capsules have to be considered as pressurised containers with thin walls within the scope of isotropic linear elasticity. The pressure which inflates the shell is then given by:

$$P = \frac{2E}{1-v} \cdot \frac{h}{R} \cdot \frac{u(R)}{R},$$

wherein u(R) is the radial displacement at a distance $R_{in}$≤R-≤$R_{out}$ from the centre of the capsule, and v is the Poisson ratio (Landau, L. D., et al 1986, Theory of Elasticity, Third Edition: Volume 7. Butterworth-Heinemann). The slow reduction of h(t) observed (FIG. 12A, symbols) is compliant with a 1/$R^2$ dependency (FIG. 12A, lines), as expected for an incompressible gel (v=½). In practice, the experimental conditions require additional corrections. First of all, for thin capsules, the assumption of linear elasticity cannot be applied given that the deformations exceed 20%. A phenomenological dependency of Young's modulus on the deformation has to be taken into account for non-linear elasticity (see Example 5 point M.). Next, for thick capsules (h/R of about 0.25), the complete formalism of the theory of a container with thick walls has to be used (see Example 5 point N.). Taking into account these corrections, the inventors observed that the pressure curves of thin and thick capsules mainly drop within the experimental error (FIG. 12B) and exhibit two main characteristics. First of all, the pressure rapidly accumulates during the first 24 hours after confluence (FIG. 13B, $\dot{P}$=2.4±0.5 kPa (day)$^{-1}$). Next, at a threshold pressure $P_{th}$=2.2±0.5 kPa, the transition in phase 3 is indicated by a dramatic drop in the increase of the pressure, which attains a constant value as low as $\dot{P}$=0.2±0.08 kPa (day)$^{-1}$ (FIG. 13B). The single fact that $\dot{P}$ remains positive indicates that the growth of the spheroids is not interrupted, as confirmed by the resumption of rapid growth after dissolution or bursting of the capsule (FIG. 11A and FIG. 14). On the whole, these results demonstrate that the mechanical characteristics of the confined spheroids may be characterised from a quantitative point of view by measuring the deformation of the elastic capsules. On the other hand, in order to obtain a mechanistical understanding of an altered MCS growth under confinement conditions, it is necessary to study the outcome of post-confluence spheroids at a cell and molecular level.

II.D Impact of Elastic Confinement on the Internal Cell Organisation of the Spheroids As aforementioned, the post-confluence stages of the MCSes are characterised by the clear occurrence of a dark core. The reorganisation of the structure of the MCS seems to be concomitant with the occurrence of phase 3 (FIG. 13C). In order to elucidate the cause of this significant transparency loss of the core of the MCS, the inventors used fluorescent colouring agents non-permeable to the membranes. First of all, they used an agent for staining hydrosoluble proteins, sulforhodamine B (SRB), which accumulates in the extra-cellular space (permeabilised cells or secreted proteins). By two-photon microscopy, the inventors observed that i) a pale core is nucleated a few hours after confluence (at P of about 0.5 kPa), ii) it propagates towards the outside in a fractal type way (as far as $P\sim P_{th}$), and iii) at subsequent moments overtime, the marked core occupies the largest fraction of the spheroid while the 3-4 first peripheral cell layers remain colourless (data not shown). As a control, a spheroid of the same size (R~150 μm), cultivated in a larger capsule and released before confluence, the difficulty reveals any colouration. The organisation of the core sensitive to the SRB colouring agent is for example only induced by the confinement and is not comparable with the formation of the necrotic core observed in larger spheroids (R>400 μm), resulting from limited diffusion of oxygen and nutrients. Next, the inventors acquired encapsulated MCS images marked with a colouring agent sensitive to the membranes, FM4-64. Given that the fluorescence of FM4-64 is more intense in a lipophilic environment, the nuclei of living cells are negatively coloured. The necrotic events are revealed by the occurrence of strong fluorescence in the integrality of the cell. The similarity between the profiles of SRB and of FM4-64 confirms that the core induced by the confinement consists of permeabilised cells or cell debris. Nevertheless, an immunocolouration of fixed post-confluence MCSes also reveals the presence of fibronectin (data not shown), which suggests that the core consists in a mixture of dead cells and secreted proteins of the matrix. This nature of the core of the mixture type is consistent with its strong apparent cohesion given that it resist to dissociation following a treatment with trypsin (data not shown).

The imaging of the core of an MCS is a difficult task because of the restricted diffusion of extrinsic colouring agents and of the limited penetration depth of light. On the other hand, the border of the compressed cells between the shell and the core is further sensitive to high-resolution microscopy of living cells. The inventors have obtained images of CT26 cells stably transfected with LifeAct-mCherry for 3 days before and after confluence (data not shown). At the start, the cells are relatively rounded and moderately mobile within the expanding spheroid. Once the confluence is reached, most of the peripheral cells exhibit significant migration and form long and thin protrusions with lamellopodia and filopodia at the ends. Lamellopodia and filopodia were also observed in non-transfected fixed cells coloured with fluorescent phalloidin (data not shown).

On the whole, these imaging data suggests that confinement induced by the capsule causes reorganisation within the spheroid after confluence, which assumes a layered structure at equilibrium consisting of a compact core consisting of cell debris cemented by extra-cellular proteins such as fibronectin, elastin, and a peripheral border of highly motile elongated cells.

Example 6: Encapsulation of CT26 Cells in a Simple Alginate Capsule

I Experimental Conditions
I. A. Encapsulation

The encapsulation of the cells is achieved by forming a jet consisting of two co-axial phases. The internal phase containing the suspended cells in their culture medium, or an iso-osmotic biological buffer compatible with the encapsulation method; this phase will compose the core of the capsules. The external phase consists of a dispersion of sodium alginate at 2% m/v having an L-guluronic/D-mannuronic (G/M) ratio comprised between 65-75%/25-35% and a viscosity for a 1% m/v dispersion at 20° C. comprised between 200 and 400 mPa·s. (i.e. FMC BioPolymer, Protanal LF 200S) and 0.5 mM of sodium dodecyl sulfate (SDS). The external phase will produce in fine the alginate shell of the capsule. Each of the phases is placed in a sterile syringe, the flow rate of which is controlled by a syringe pump. The syringes are connected to a two-way injector schematised in FIG. 15A, giving the possibility of producing a jet. According to this schematic illustration, the internal phase intended to be encapsulated circulates through the compartment 21 so as to be injected in the centre of the capillary C. The external phase intended to form the alginate shell of the capsule circulates through the compartment 41 and is injected at the internal periphery of the capillary C.

The flow rates delivered by the syringe pumps depend on the geometry of the injector, notably on the diameter of the outlet capillary, and on the viscosity of the fluids used. These flow rates are adapted so as to allow the formation of a jet (passing from the drop-wise conditions to a jet) for which the fragmentation in microdroplets is accomplished according to the Plateau-Rayleigh instability. This fragmentation may be controlled by applying to the fluid of the external phase a vibration controlled by a piezo-electric effect with a frequency located between 0 and 2000 Hz. In order to prevent coalescence of the microdroplets formed, a cylindrical electrode is placed at the fragmentation site of the jet; a DC current under 0 to 2000 V is applied and has the effect of electrically charging the surface of the microdroplets thereby ensuring their respective repulsion and preventing their coalescence.

The multi-component microdroplets formed during the fragmentation of the jet, under the effect of gravity, fall into an aqueous solution of 1% (m/v) calcium chloride which has the effect of cross-linking the alginate outside the microdroplets and of thus forming the alginate shell containing in its core the cells of the internal phase. The capsules are reenvelopeed, rinsed in a physiological buffer not depolymerising the alginate (i.e. without any phosphates or chelating agents) and then placed in sterile cell culture flasks with the culture medium used for the cells. The alginate shell of the capsules being semi-permeable, it allows diffusion of the nutrients and of the gases required for cell survival and growth. The capsules are incubated at 37° C. and with 5% of $CO_2$ in order to allow the growth of the cells.

I.B. Cell Survival and Growth

The cells used are tumoral cells of the CT26 line.

As the alginate capsules are optically transparent, the encapsulated cells in a first phase were observed in optical microscopy in order to determine their morphology and to follow their evolution.

Cell survival may be determined by using conventional colorimetric methods (e.g. MTT, XTT, Resazurin tests) or fluorimetric methods (calcein, fluorescein diacetate, propidium iodide) based on the metabolism and cell physiology.

In this case, simple cell survival of the cells encapsulated in capsules was carried out by marking with calcein and with propidium iodide, was carried out on newly formed capsules according to the following method. The capsules are incubated in the presence of an esterified form of calcein (Calcein-AM, LifeTechnologies) not fluorescent under the conditions prescribed by the manufacturer. This fluorophore diffuses through the capsule and through the plasma membrane and is hydrolysed within cells for which the metabolism is active (i.e. living); the thereby produced calcein is fluorescent in green and remains, because of its charge, in the cytosol of the cells. After incubation of the capsules with calcein-AM, the capsules are put into contact with propidium iodide. This fluorophore, because of its charge, only diffuses into the cells for which the plasma membrane is damaged and binds onto the DNA, which has the effect of increasing its fluorescence by 20 to 30 times. Thus, after exposure of the capsules to these two fluorophores, the observation of the cells under confocal microscopy gives the possibility of distinguishing the living cells, which are fluorescent in green, from dead cells, which are fluorescent in red.

II. Results

The cell viability was controlled by means of the Live/Dead test at D0 and at D15 after the encapsulation showing very good cell survival thus, the cells survive to encapsulation and have good cell growth beyond 15 days.

The observation of the capsules in optical or confocal microscopy confirms the formation of spheroids, i.e. cell aggregates. Such structures are observed with tumoral cells which do not adhere to the walls of the capsule. These capsules are therefore good models for studying metastasis.

These capsules are particularly advantageous for cultivating non-adherent suspended cells such as blood cells.

Example 7: Three-Dimensional Cultivation of Skin Tissue in Structured Alginate Capsules In order to go beyond simple co-cultivation of cells in alginate capsules, the capsules may be incubated for several days under conditions allowing cell proliferation and then the organisation of the cells into tissue(s) similar to skin tissues. Thus, the fibroblasts disseminated in the intermediate envelope may, depending on the cultivation conditions, proliferate and then synthesise molecules of the extracellular matrix. This organisation corresponds to the organisation of the dermis of the skin tissue. Also, the keratinocytes contained in the core of the capsule are intended to adhere to the internal surface of the intermediate envelope, in the core, proliferate until a cell monolayer is organised covering the inside of the capsule. Upon completion and under defined cultivation conditions, the keratinocytes may enter differentiation and form a cohesive stratified tissue similar to the keratinised stratified epithelium forming the epidermis of the skin tissue.

Thus, it is possible to form capsules independently containing reconstructed dermis, reconstructed epidermis and reconstructed skin, and association of the dermis and of the epidermis reconstructed within a same capsule.

I. Experimental Conditions

IA. Collagen

During the development of SkinPearls, several types of collagen were tested. Depending on the extraction methods used, the solutions of collagens are not all capable of forming a gel. As an indication, Collagen I stemming from rat tails from Gibco at 3 mg/ml and the Collagen solution stemming from bovine skin at 3 mg/ml from Sigma allow the formation of a gel.

The gelling kinetics of the collagen solution is increased by the combined effect of the neutralisation of the pH and a rise in the temperature to 37° C. Indeed, collagen is soluble in an acid aqueous solution, generally of acetic acid, and the neutralisation of the pH allows regeneration of the electrostatic interactions between the collagen fibrils in order to form structured fibres within a lattice.

In parallel, collagen was extracted from rat tails according to the following procedure. Briefly, two rat tails soaked beforehand in 70° ethanol were dissected and the tendons were extracted from their fascia. These tendons were then soaked in acetic acid solutions placed at 4° C. regularly stirred until solubilisation. The solutions having become thicker are then centrifuged several times in order to remove the present debris. The supernatents are kept at 4° C. until use. This collagen actually forms a gel when its pH is neutralised and it was substituted for the commercially available collagen for developing skin model capsules.

Procedure for Neutralising the pH

Typically, a buffer with a high ionic force is prepared and then mixed with collagen. The different buffers are added in this order. Each of the solutions, stored at 4° C., is kept in ice in order to maintain the whole at 4° C. and thereby slow down the formation of the gel.

| Buffer | Concentration/pH | Volume (μL) (Vf = 2 mL) |
| --- | --- | --- |
| HEPES | 200 mM/7.5 | 200 |
| MEM | 10X | 200 |
| DMEM | 1X/7.4 | 256 |
| NaOH | 1M | 21 |
| Collagen | 3 mg/mL/3.6 | 1333 |

Marking the Collagen with Rhodamine

When making three-dimensional culture capsules and more specifically the intermediate envelope forming the capsules, it is interesting to be able to observe the morphology of this layer. Indeed, many factors may have an impact on its formation and it is important to understand the parameters which control its length, its homogeneity as well as its geometry. For this, collagen was marked with a fluorophore, Rhodamine, in order to be able to produce 3D images of the capsules in confocal microscopy. Briefly, 0.2 mg of rhodamine isothiocyanate (RITC) per ml of collagen are incubated at 4° C. away from light for 48 hours. At the end of this incubation, the collagen is dialysed against an aqueous solution of 0.05M acetic acid in order to remove the excess rhodamine. The collagen marked with rhodamine is diluted in a non-marked collagen when this is necessary. This marking has not shown any negative effect on the polymerisation of the collagen.

I.B Alginate

The capsules are formed from an alginate solution (Protanal LF 200S, FMC) at 2% w/v and of 0.5 mM SDS filtered beforehand to 0.8 µm. This solution is supplemented with a Streptomycin/Penicillin mixture at 50 U/mL and kept at 4° C. in order to limit development of microorganisms.

The alginate solution used for partly or totally producing the intermediate envelope is a 1% w/v solution, without any SDS, also filtered to 0.8 µm before use.

I.C Buffers

The capsules are formed in a 1% calcium chloride bath filtered to 0.2 µm, in the presence of a drop of Tween 20 in order to modify the surface tension at the surface of the bath and to optimise the formation of round capsules. In order to remove the excess calcium ions, the capsules, immediately after formation, are rinsed in a HEPES buffer (300 mOsm, pH=7.5) prepared from a Hepes 5× solution (119.15 g Hepes, 3.75 g of NaOH tablets, water qsp 500 mL, pH adjusted to 7.5). Indeed, the buffer used should be compatible with cell survival and should not depolymerise the alginate as this is the case with phosphate or citrate buffers.

I.D Cell Culture

The human dermis fibroblasts come from plastic surgery waste. These cells are cultivated in cell culture flasks of 75 cm$^2$, in the presence of DMEM (LifeTechnologies) supplemented to 10% v/v with foetal calf serum (FCS, LifeTechnologies). The passages are achieved at 80-90% confluence, 2 to 3 times a week.

The keratinocytes come from adult human epidermis from plastic surgery waste. These cells are cultivated on 75 cm$^2$ cell culture flasks coated beforehand with collagen of type I from rat tails. The keratinocytes are cultivated in an Epilife medium (LifeTechnologies) completed with Epilife Defined Growth Supplement (EDGS, LifeTechnologies). The passages are achieved at 70-80% confluence and the medium is renewed every two days.

In order to achieve the passages, the culture media are removed beforehand, the cell coat is rinsed with 3 mL of 0.05% Trypsin solution (LifeTechnologies) discarded immediately and then renewed. The flasks are then placed in the incubator for a few minutes so that the cells are detached from the surface. The trypsin is then neutralised by adding 5 ml of trypsin inhibitor (LifeTechnologies). The cell suspension is then centrifuged (180 g, 8 min) and then the sediment is dispersed in 1 ml of the culture medium corresponding to the cell type. This suspension is then used for seeding new flasks, with a ratio of 3 sown flasks for 1 flask at 80% confluence.

I.E Preparation of the Cells for Encapsulation

The cells are treated like during a passage. Once the cell suspension is obtained, the cells are counted by means of counting cells (i.e. KovaSlide) by conducting an exclusion test with trypan blue. Only living cells not marked with trypan blue, are counted. The fibroblasts intended to be localised in the intermediate envelope of the capsules will be dispersed in the phase of the intermediate envelope, described hereafter, in an amount from 0.3 to 0.75 M of cells per ml. The keratinocytes, intended to be encapsulated in the core of the capsules are dispersed in the culture media or the biological buffer in an amount from 0.5-1.5 M of cells/ml.

I.F Preparation of the Intermediate Envelope

The reconstruction of a skin tissue within alginate capsules requires the possibility of compartmentation of these capsules into two areas corresponding to the two sheets making up the skin, i.e. the epidermis and the dermis. From the physico-chemical point of view, the intermediate envelope, at the interface between the alginate shell and the core of the capsule, should have a composition for which the viscosity is less than that of the phase forming the alginate envelope and greater than that of the phase intended to form the core of the capsule. Further, its composition should allow cross-linking or rapid polymerisation during the formation of the capsules in order to prevent flow phenomena and therefore disorganisation of the structure. From the biological point of view, the composition of the intermediate envelope should allow survival and growth of fibroblasts which will be disseminated in its interior, thereby regenerating a matrix similar to the dermal matrix. Finally, the composition of the intermediate envelope should allow adhesion of the keratinocytes to its surface.

In order to solve the whole of these constraints, the intermediate envelope consists of 50 to 80% of Matrigel (BD Biosciences), or 50 to 80% of collagen of type I (Gibco) the pH of which is extemporaneously neutralised by adding a biological buffer and sodium hydroxide. The polymerisation of these matrix compounds being insufficiently rapid, 20 to 50% of a 4% w/v sodium alginate solution are added. Finally, the fibroblasts are dispersed in this mixture in order to obtain a cell concentration comprised between 0.3 and 0.75 M of cells/ml.

I.G Formation of the Capsules

The capsules are formed by fragmentation of a jet as described earlier with modifications in order to allow structuation of the capsules. For this, a 3-way injector is used (FIG. 15B). The internal phase forming the core of the capsule circulates in a first compartment 21 and is injected to the centre of the capillary C. This internal phase is cladded with the intermediate phase circulating in the compartment 31 and which will form the intermediate envelope of the capsule. The external phase circulating in the compartment 41 is intended to form the alginate shell of the capsule and is injected at the internal periphery of the capillary C. Each of the routes 21, 31 and 41 is injected into the outlet capillary C and is intended to form, from the outside to the inside, the alginate shell, the intermediate envelope and the core of the capsule. The flow rate of each of the routes is controlled by an electric syringe pump. The syringe of the internal phase is also equipped with a magnetic system allowing homogenisation of the cell suspension, without shearing, in order to avoid sedimentation of the cells and to ensure homogeneity during the handling. The fragmentation of the jet and the coalescence of the microdroplets may be controlled by piezo-electric vibration and formation of an electric field respectively. The capsules formed are covered as described earlier and then incubated at 37° C. with 5% $CO_2$.

The type of produced capsule depends on the type of cells present. The capsules for skin models contain both fibroblasts in the intermediate envelope and keratinocytes in the core. The capsules for the epidermis models only contain keratinocytes in the core while the capsules for dermis models only contain fibroblasts in the intermediate envelope.

I.H Morphology of the Capsules

After formation, the capsules are directly observed in suspension in the culture medium by means of an inverted microscope. The shape of the capsules (i.e. circularity) and the polydispersity of the sizes are determined by calibrating micrographs acquired with this microscope. Also, the distribution of the cells within the capsule and their localisation within the intermediate envelope and within the core of the capsules are also checked.

I.I Structure of the Capsules

In order to check the organisation of the different layers of the formed capsules, the marking of the intermediate envelope is achieved by substituting a portion of the collagen of the composition with collagen marked with rhodamine B, a fluorescent marker. After forming the capsules according to the method described earlier, the three-dimensional distribution of the intermediate envelope is determined by acquiring images in confocal microscopy on the whole of the capsule.

I.J Characterisation of the Cell Viability and Proliferation

Cell viability is determined by imaging the capsules marked with calcein and propidium iodide according to the method described earlier. The monitoring is carried out over several days in order to determine the evolution of the proliferation and of the organisation of the cells.

II Results

II.A Three-dimensional culture: Dermis model

The capsules according to the invention were used in order to set into place models of reconstructed dermis. Thus, these capsules contain fibroblasts disseminated in a matrix which is desirably as close as possible to the dermis. The dermis is a connective tissue rich in collagen, elastin, fibronectin and glycosaminoglycan which gives it its mechanical properties. The dermis produces a supporting and nutrient tissue for the epidermis: indeed as the epidermis is avascular, the nutrients and the gas exchanges essentially come from the dermis. The main cells of the dermis are fibroblasts; disseminated in the matrix, they sustain its composition and play an important role during healing phenomena. Moreover, fibroblasts secrete cytokines and growth factors which stimulate and regulate the proliferation of keratinocytes. Also, the dermal matrix has a particular composition promoting adhesion of the keratinocytes of the epidermis and regulating their proliferation and differentiation. Cosmetically, the dermis is the target of anti-ageing treatments: the maintaining and stimulation of the synthesis of the components of the extracellular matrix is the main target of an anti-wrinkle treatment.

Capsule with a Single Envelope

In a first model, the fibroblasts were encapsulated within the alginate envelope making up the external envelope of the capsule. The goal, in fine, is to contain these cells in this compartment, to produce an intermediate layer with a specific composition for promoting adhesion of the keratinocytes in the core of the capsule. However, after encapsulation of the fibroblasts and the carrying out of a survival test (of the Live/Dead Calcein-AM Type and propidium iodide), it appears that all the cells are dead, none seem to survive. This toxicity is due to the presence in the alginate of sodium dodecyl sulfate (SDS) in an amount of 0.5 mM. The SDS is essential for forming the capsules and the concentration used is the lower limit below which it is no longer possible to form homogenous capsules. Now, the establishment of a cytotoxicity test demonstrates the cytotoxic effect of SDS towards fibroblasts and notably towards the 3T3 line. Thus, the inventors have shown that between 0.05 mM and 0.4 mM of SDS in the culture medium, the cell survival is between 75 and 100%, it is lowered to 38% with 0.5 mM of SDS. Consequently, this SDS concentration causes the death of more than 60% of the cells. It is not possible to remove the SDS, however the fibroblasts may be encapsulated directly in the intermediate envelope. This option provides the possibility of allowing a modification of the composition of the latter in order to approach as close as possible to that of the dermal extracellular matrix.

Capsule with an Intermediate Alginate Envelope

The capsules according to this alternative comprise cells only in the intermediate envelope. In a first phase, the inventors produced capsules for which the intermediate envelope consisted of a 1% w/v alginate dispersion containing fibroblasts from the 3T3 line in an amount of $0.75 \cdot 10^6$ cells/ml. Different flow rates of each of these phases forming the different layers of the capsules were tested, and once rinsed, the capsules are suspended in the full culture medium and placed in the incubator at 37° C. with 5% $CO_2$. Cell viability was controlled by means of the Live/Dead test at D0, D2, D6 and D28 after encapsulation during this test the living cells are marked with calcein and the dead cells with propidium iodide. The acquisition of the signal of the cells through the capsules is carried out by confocal microscopy. The inventors have thus shown that a portion of the cells is dead after encapsulation, because of the stress caused by the enzymatic treatment for their detachment from the culture flasks but also by the shearing during their mixing with the alginate and during the formation of the capsules. However, a portion of the cells remains alive up to one month after encapsulation. The inventors observed that the cells proliferate but remain restricted to a few areas of the capsule in the form of spheroids or rods. This is due to the fact that the fibroblasts do not secrete any enzymes capable of lyzing the alginate thereby preventing any progression of the cells through the alginate network. The cells proliferate by filling the defects present in this matrix.

Capsule with an Intermediate Collagen Envelope

The same experiment was conducted by substituting the intermediate alginate envelope with a collagen layer. The capsules according to this alternative also comprise, cells only in the intermediate envelope. The collagen is one of the major components of the dermal extracellular matrix and may be degraded by the collagenases secreted by the fibroblasts. Cell viability was monitored by means of the Live/Dead test at D0, D4, D8, D15 and D19 after encapsulation during this test, the living cells are marked with calcein and the dead cells with propidium iodide. The results show that in this case, very good cell survival, spreading out of the cells and rapid proliferation covering the integrality of the capsule.

The fibroblasts in this case rapidly proliferate which may be a problem during the formation of skin model capsules subsequently because the keratinocytes proliferate more slowly. Indeed, the keratinocytes take between 14 and 21 days for forming the different layers which make up the epidermis. Thus, the proliferation of the fibroblasts should be controlled. For this, the inventors tested different compositions of intermediate layer by mixing different proportions of alginate and of collagen. As an example, the inventors showed that the growth of fibroblasts within an intermediate layer half consisting of 1% w/v alginate and for the other half collagen is limited to growth in the form of sheets.

Thus, cell viability was monitored by means of a Live/Dead test at D0 and D15 after encapsulation showing very good cell survival. Further, at D0, the collagen marked with RITC is visible, at D15 only the fluorescent signals of the living and dead cells are recorded demonstrating that the whole of the collagen is lyzed by the fibroblasts during their growth.

As a conclusion, it is possible to control the proliferation and the distribution of the fibroblasts by modifying the composition of the intermediate envelope where the cells are localised and more particularly on the ratio between alginate and collagen.

These parameters were characterised by using fibroblasts from the murine line 3T3. In order to determine the viability of this model for subsequent applications, dermis models were produced from fibroblasts of adult human dermis (HDFa). The culture of HDFa cells by the inventors in capsules with an intermediate envelope of collagen shows that the cells survived encapsulation, adhere and rapidly spread out onto the intermediate collagen envelope. Further, the cell viability test (Live/Dead test at D0 and D5 after encapsulation) shows very good cell survival, validating this model for future optimisation and development.

Capsule with an Intermediate Envelope with an Alginate/Collagen Mixture

The same experiment was conducted by substituting the intermediate alginate envelope with a layer comprising 25% of alginate for 75% of collagen.

Morphology of the capsules: The capsules formed according to the method described above are spherical, their smooth external surface and with a diameter neighbouring 500-600 µm depending on the flow rates used and on the diameter of the capillary at the outlet of the injector. The cells are absent from the external alginate layer forming the capsule and are restricted to the intermediate layer consisting of a collagen solution, for which the pH was neutralised at 0.2% m/v (75%) and of a 1% m/v alginate solution (25%), slightly more dense optically, as well as in the core of the capsules.

Organisation of the intermediate layer: The intermediate layer may be viewed inside the capsules by confocal imaging of the collagen marked with a fluorophor. The acquired images show a distribution of the collagen of the structured intermediate layer in a homogenous layer through the capsules, coating the inside of the latter and delimiting a liquid core.

Characterisation of the cell viability and proliferation: Cell viability was directly characterised after encapsulation but also after several days of cultivation in an incubator at 37° C. and with 5% of $CO_2$. The majority of the cells give a green signal and therefore have active metabolism. A few cells give a red signal expressing membrane permeability, therefore a dead cell. On the whole, more than 80% of the cells are viable after encapsulation. After several days of incubation, the cells proliferate and become organised and less and less distinguishable. Proportionally, the living cells remain a majority.

II.B Three-Dimensional Culture: Epidermis Model

The epidermis is a keratinised stratified epithelial tissue. The keratinocytes are the main cells of this tissue. In vivo, the most basal layer, in contact with the dermo-epidermal junction (DEJ) separating the dermis from the epidermis, is the germinative layer. This layer ensures renewal of the surface layers by stimulating the proliferation of keratinocytes. Once the cells lose their contacts with the DEJ, they initiate their differentiation into corneocytes. This cell specialisation ensures strong cohesion forming the epidermal barrier mainly supported by the most external layer: the stratum corneum. Thus, in order to initiate the formation of an epidermis in the capsules according to the invention, a matrix promoting the adhesion of keratinocytes, their proliferation into a confluent layer which will initiate stratification, should be produced. The final keratinisation steps further require a stimulus related to contact with air. Thus, the epidermis models according to the invention, in the absence of the stimulus will only be able to exhibit an epidermis having not completed its terminal differentiation. The capsules according to this alternative comprise cells only in the liquid core.

Collagen is a substrate of choice for adhesion of keratinocytes. In a first phase, the inventors produced capsules with an intermediate layer exclusively made of collagen, the keratinocytes of the HaCaT line are present in the liquid core. Marking the keratinocytes with calcein shows that the keratinocytes survive encapsulation (at D0), adhere to the collagen matrix (at D5) and proliferate by forming "patches" (at D16), sheets of cohesive cells, which gradually invade the internal surface of the capsule.

Thus, when the intermediate layer exclusively consists of collagen, the structure of the collagen matrix becomes heterogeneous during its gelling inducing cell adhesion in plates of cells. Indeed, during encapsulation, the dispersion of collagen for which the pH was neutralised begins to gel thereby modifying its viscosity. Further gelling is not instantaneous as may be the cross-linking of the alginate in contact with calcium ions. Thus, collagen slips from the walls of the capsule and piles up at the bottom of the latter before totally gelling, or to a lesser extent, generates instabilities at the origin of mixtures of suspended cells in the core with the collagen.

In order to find the remedy to the problems related to the gelling kinetics of collagen, the inventors mixed the collagen with alginate, this having the purpose of generating a template for the gelling of collagen. In a first phase, the inventors determined the ratios of alginate and of collagen which favoured adhesion of the keratinocytes of the HaCaT line. For this alginate gels with increasing collagen concentrations (0%, 0.05%, 0.1%, 0.15% and 0.2% m/v) and decreasing alginate concentrations (1%, 0.75%, 0.5%, 0.25% and 0% m/v) were produced, and then sown with keratinocytes. The control is the adhesion of the cells, under the same conditions to the plastic treated for cell culture. After a few hours, the cells were observed in optical microscopy. The non-adherent cells are perfectly round and refringent while the adherent cells spread out and have a polyhedril shape. FIG. 14 shows these observations.

From these observations, it appears that the adhesion of the keratinocytes begins as soon as 25% v/v of collagen solution in the alginate (final collagen concentration of 0.05% m/v) while these cells are incapable of adhering to the pure alginate gel. The more the collagen content increases, the more the cells are adherent and spread out. Capsules for which the intermediate layer contained a mixture of alginate and of collagen in order to promote adhesion of the keratinocytes were produced with alginate/collagen 0.5% m/v/0.1% m/v, 0.25% m/v/0.15% m/v, 0% m/v/0.2% m/v.

Marking of the keratinocytes with calcein shows that the keratinocytes survive encapsulation (at D0), adhere to the matrix (at D5) for the whole of the capsules. Nevertheless, the cells adhere and better proliferate (D16) in the presence of collagen alone.

It seems that for an equal mixture of alginate solutions (1% m/v) and of collagen solutions (0.2% m/v), the cells adhere very little and a lot of them die. The centripetal cross-linking of the alginate is able to organise the collagen in a particular way and in a less favourable way to the cells comparatively with the observations made on a gel in a culture dish. In the presence of larger volumes of collagen solution (corresponding to final concentrations of collagen from 0.15 to 0.20% m/v), the keratinocytes adhere and proliferate but remain confined to isolated patches after 16 days of cultivation. The distribution of the collagen of the intermediate layer is not homogenous which does not allow the keratinocytes to migrate over the whole of the internal surface of the capsule. In order to resolve this distribution, for an equal concentration of collagen, the final concentration of alginate may be increased to 1.0% m/v allowing better stiffness of the intermediate layer and better distribution of the collagen.

The invention claimed is:

1. A microcapsule comprising:
   a liquid core;
   a stiff intermediate envelope comprising at least one biopolymer; and
   at least one external envelope totally encapsulating the liquid core at its periphery,
   said intermediate envelope being located between the liquid core and the external envelope,
   said external envelope being able to retain the liquid core when the microcapsule is immersed in a gas and comprising at least one gelled polyelectrolyte and/or one stiffened biopolymer,
   said microcapsule further comprising at least one eukaryotic mammalian cell, wherein the liquid core comprises at least one keratinocyte and the intermediate envelope comprises at least one fibroblast; and
   said stiff intermediate envelope having an elastic modulus that is non-zero.

2. The microcapsule according to claim 1, wherein the biopolymer of said intermediate envelope is selected from the group consisting of proteins of the extra-cellular matrix, proteoglycans, glycosaminoglycans, polysaccharides, and non-hydrolysed or partly hydrolysed form thereof.

3. The microcapsule according to claim 1, wherein the microcapsule is obtained by a method comprising the following steps:
   a) forming a multi-component liquid drop comprising:
      a liquid core,
      a liquid intermediate envelope formed with an aqueous composition comprising at least one biopolymer, totally encapsulating at its periphery the liquid core, and
      a liquid external envelope formed with an aqueous composition, different from the intermediate composition, said aqueous composition comprising at least one polyelectrolyte and at least one surfactant, said liquid external envelope totally encapsulating at its periphery the intermediate envelope,
      the liquid core and/or the liquid intermediate envelope comprising at least one eukaryotic mammalian cell as set forth in claim 1,
   b) gelling by immersion of said multi-component liquid drop in a gelling solution containing a reagent capable of gelling the polyelectrolyte of the liquid external envelope, in order to obtain a gelled microcapsule comprising a gelled external envelope,
   c) stiffening the intermediate composition of the liquid intermediate envelope, in order to obtain a gelled and stiffened microcapsule comprising a stiffened intermediate envelope, said stiffened intermediate envelope having an elastic modulus that is non-zero, and
   d) recovering said gelled and stiffened microcapsules.

4. The microcapsule according to claim 3, the method further comprising a step for dissolving the gelled external envelope.

5. A method for preparing the microcapsule according to claim 1, the method comprising the following steps:
   a) forming a multi-component liquid drop comprising:
      a liquid core,
      a liquid intermediate envelope formed with an aqueous composition comprising at least one biopolymer, totally encapsulating at its periphery the liquid core, and
      a liquid external envelope formed with an aqueous composition, different from the intermediate composition, said aqueous composition comprising at least one polyelectrolyte and at least one surfactant, said liquid external envelope totally encapsulating at its periphery the intermediate envelope,
      the liquid core and/or the liquid intermediate envelope comprising at least one eukaryotic mammalian cell as set forth in claim 1,
   b) gelling by immersion of said multi-component liquid drop in a gelling solution containing a reagent capable of gelling the polyelectrolyte of the liquid external envelope, in order to obtain a gelled microcapsule comprising a gelled external envelope,
   c) stiffening the intermediate composition of the liquid intermediate envelope, in order to obtain a gelled and stiffened microcapsule comprising a stiffened intermediate envelope, and
   d) recovering said gelled and stiffened microcapsules.

6. The method according to claim 5, wherein the method further comprises a step for dissolving the gelled external envelope.

7. An in vitro method for cultivating eukaryotic mammalian cells comprising:
   a) cultivating a microcapsule under sufficient conditions for cell growth, said microcapsule comprising a liquid core, and at least one external envelope totally encapsulating the liquid core at its periphery,
   said external envelope being able to retain the liquid core when the microcapsule is immersed in a gas and comprising at least one gelled polyelectrolyte and/or one stiffened biopolymer, said microcapsule further comprising at least one eukaryotic mammalian cell as set forth in the preparation method according to claim 5; and
   b) harvesting said microcapsule.

8. A method for screening active ingredients comprising:
   a) cultivating the microcapsule according to claim 1 in the presence and in the absence of a candidate substance,
   b) detecting a phenotype of interest in the cells of the microcapsule cultivated in the presence of the candidate substance as compared with the cells of the microcapsule cultivated in the absence of the candidate substance, and
   c) identifying the candidate substance as an active ingredient if a phenotype of interest has been detected.

9. The method according to claim 8, wherein the active ingredient is a cosmetic active ingredient.

10. An in vitro method for cultivating eukaryotic mammalian cells comprising the following steps:
    a) cultivating the microcapsule according to claim 1 under sufficient conditions for cell growth, and
    b) harvesting said microcapsule.

11. The method according to claim 10, wherein said eukaryotic mammalian cells are human cells.

12. The microcapsule of claim 1, wherein the stiff intermediate envelope is obtained by a stiffening method selected from the group consisting of: polymerization, precipitation, colloidal aggregation, and a glassy transition caused by a variation in temperature.

13. The microcapsule of claim 1, wherein the stiff intermediate envelope is obtained by coacervation of an intermediate composition of a liquid intermediate envelope formed with an aqueous composition comprising at least one biopolymer.

\* \* \* \* \*